(12) United States Patent
Davies

(10) Patent No.: US 8,280,504 B2
(45) Date of Patent: *Oct. 2, 2012

(54) METHOD AND SYSTEM FOR DETECTING ELECTROPHYSIOLOGICAL CHANGES IN PRE-CANCEROUS AND CANCEROUS TISSUE

(75) Inventor: Richard J. Davies, Saddle River, NJ (US)

(73) Assignee: EPI-SCI, LLC, Saddle River, NJ (US)

( * ) Notice: Subject to any disclaimer, the term of this patent is extended or adjusted under 35 U.S.C. 154(b) by 1113 days.

This patent is subject to a terminal disclaimer.

(21) Appl. No.: 11/096,665

(22) Filed: Apr. 1, 2005

(65) Prior Publication Data
US 2005/0203436 A1     Sep. 15, 2005

Related U.S. Application Data

(62) Division of application No. 10/151,233, filed on May 20, 2002, now Pat. No. 6,922,586.

(51) Int. Cl.
*A61B 8/00* (2006.01)
*A61B 5/02* (2006.01)
*A61B 5/05* (2006.01)
*A61N 1/30* (2006.01)

(52) U.S. Cl. ........ 600/547; 600/442; 600/506; 600/554; 604/20

(58) Field of Classification Search .................. 324/554; 600/442, 506, 536, 547, 554; 604/20
See application file for complete search history.

(56) References Cited

U.S. PATENT DOCUMENTS 3,786,801 A * 1/1974 Sartorius ...................... 600/573
3,949,736 A    4/1976 Vrana et al.
4,291,708 A * 9/1981 Frei et al. ...................... 600/547
4,458,694 A * 7/1984 Sollish et al. ................. 600/547
4,486,835 A * 12/1984 Bai et al. ......................... 378/21

(Continued)

FOREIGN PATENT DOCUMENTS

WO    WO-98/23204 A1    6/1998

(Continued)

OTHER PUBLICATIONS

Yao X, Kwan HY. Activity of Voltage-Gated K+ Channels is Associated With Cell Proliferation and Ca2+ Influx in Carcinoma Cells of Colon Cancer, Life Sciences Including Pharmacology Letters, May 1999, pp. 55-62, vol. 65, No. 1, Elsevier Science, Inc.

(Continued)

*Primary Examiner* — Sean Dougherty
(74) *Attorney, Agent, or Firm* — Lerner, David, Littenberg, Krumholz & Mentlik, LLP

(57) ABSTRACT

A method and system are provided for determining a condition of a selected region of epithelial tissue. At least two current-passing electrodes are located in contact with a first surface of the selected region of the tissue. A plurality of measuring electrodes are located in contact with the first surface of the selected region of tissue as well. Electropotential and impedance are measured at one or more locations. An agent may be introduced into the region of tissue to enhance electrophysiological characteristics. The condition of the tissue is determined based on the electropotential and impedance profile at different depths of the epithelium, tissue, or organ, together with an estimate of the functional changes in the epithelium due to altered ion transport and electrophysiological properties of the tissue.

25 Claims, 17 Drawing Sheets

U.S. PATENT DOCUMENTS

| | | | |
|---|---|---|---|
| 4,690,152 A | | 9/1987 | Juncosa |
| 4,729,385 A | * | 3/1988 | Juncosa et al. ............... 600/547 |
| 4,955,383 A | * | 9/1990 | Faupel .......................... 600/407 |
| 5,099,844 A | | 3/1992 | Faupel |
| 5,109,849 A | * | 5/1992 | Goodman et al. ............ 600/483 |
| 5,143,079 A | * | 9/1992 | Frei et al. ..................... 600/547 |
| 5,345,935 A | * | 9/1994 | Hirsch et al. ................. 600/376 |
| 5,415,164 A | * | 5/1995 | Faupel et al. ................. 600/372 |
| 5,417,222 A | * | 5/1995 | Dempsey et al. ............ 600/509 |
| 5,639,444 A | | 6/1997 | Klaveness |
| 5,697,369 A | * | 12/1997 | Long et al. .................... 600/407 |
| 5,722,404 A | * | 3/1998 | Lundback ..................... 600/387 |
| 5,766,165 A | * | 6/1998 | Gentelia et al. ................ 606/35 |
| 5,810,742 A | * | 9/1998 | Pearlman ...................... 600/547 |
| 5,823,957 A | | 10/1998 | Faupel et al. |
| 5,833,622 A | * | 11/1998 | Meathrel et al. .............. 600/511 |
| 5,906,208 A | * | 5/1999 | Ishikawa et al. .............. 128/898 |
| 6,026,322 A | * | 2/2000 | Korenman et al. ........... 600/547 |
| 6,122,544 A | | 9/2000 | Organ |
| 6,134,480 A | * | 10/2000 | Minogue ........................ 607/152 |
| 6,135,953 A | | 10/2000 | Carim |
| 6,138,044 A | * | 10/2000 | Svedman ....................... 600/387 |
| 6,148,232 A | * | 11/2000 | Avrahami ........................ 604/20 |
| 6,251,681 B1 | * | 6/2001 | Davies et al. ................... 436/64 |
| 6,308,097 B1 | * | 10/2001 | Pearlman ....................... 600/547 |
| 6,312,428 B1 | * | 11/2001 | Eggers et al. .................. 606/41 |
| 6,314,315 B1 | * | 11/2001 | Hung et al. .................... 600/547 |
| 6,328,735 B1 | * | 12/2001 | Curley et al. .................... 606/41 |
| 6,363,275 B1 | * | 3/2002 | Kaiser ............................ 600/547 |
| 6,389,305 B1 | * | 5/2002 | Deban et al. ................... 600/427 |
| 6,391,026 B1 | * | 5/2002 | Hung et al. ..................... 606/41 |
| 6,456,865 B2 | * | 9/2002 | Samson ......................... 600/376 |
| 6,471,660 B1 | * | 10/2002 | Covington ..................... 600/584 |
| 6,496,725 B2 | * | 12/2002 | Kamada et al. ................ 600/547 |
| 6,500,173 B2 | * | 12/2002 | Underwood et al. ............ 606/32 |
| 6,641,604 B1 | * | 11/2003 | Adelman et al. ................ 600/37 |
| 6,712,816 B2 | * | 3/2004 | Hung et al. ..................... 606/41 |
| 6,773,418 B1 | * | 8/2004 | Sharrow et al. ............... 604/176 |
| 6,823,203 B2 | * | 11/2004 | Jordan ........................... 600/407 |
| 6,842,264 B1 | | 1/2005 | Leyva et al. |
| 6,887,239 B2 | | 5/2005 | Elstrom et al. |
| 6,898,303 B2 | * | 5/2005 | Armato et al. ................ 382/131 |
| 6,922,586 B2 | * | 7/2005 | Davies ........................... 600/547 |
| 6,993,383 B2 | | 1/2006 | Assenheimer et al. |
| 7,077,842 B1 | * | 7/2006 | Cosman ........................... 606/41 |
| 7,223,239 B2 | | 5/2007 | Schulze et al. |
| 7,499,745 B2 | * | 3/2009 | Littrup et al. .................. 600/547 |
| 2001/0051774 A1 | * | 12/2001 | Littrup et al. .................. 600/547 |
| 2002/0006216 A1 | | 1/2002 | Armato et al. |
| 2002/0026123 A1 | | 2/2002 | Pearlman |
| 2002/0110609 A1 | | 8/2002 | Hung |
| 2002/0133151 A1 | * | 9/2002 | Hung et al. ...................... 606/41 |
| 2002/0183645 A1 | * | 12/2002 | Nachaliel ....................... 600/547 |
| 2002/0188187 A1 | | 12/2002 | Jordan |
| 2003/0010987 A1 | | 1/2003 | Banin et al. |
| 2003/0040734 A1 | | 2/2003 | Morton et al. |
| 2003/0088189 A1 | * | 5/2003 | Tu et al. ......................... 600/549 |
| 2003/0109871 A1 | * | 6/2003 | Johnson et al. ................. 606/42 |
| 2003/0170840 A1 | | 9/2003 | McDonald et al. |
| 2003/0187366 A1 | * | 10/2003 | Hashimshony ............... 600/547 |
| 2003/0216661 A1 | | 11/2003 | Davies |
| 2004/0133122 A1 | | 7/2004 | Pearlman |
| 2004/0152997 A1 | | 8/2004 | Davies |
| 2004/0253652 A1 | | 12/2004 | Davies |
| 2005/0059928 A1 | | 3/2005 | Larsson |
| 2005/0203436 A1 | | 9/2005 | Davies |

FOREIGN PATENT DOCUMENTS

| | | |
|---|---|---|
| WO | 9923945 | 5/1999 |
| WO | 0035357 | 6/2000 |
| WO | 0232335 | 4/2002 |

OTHER PUBLICATIONS

Wissenbach U, Niemeyer BA, Fixemer T, Schneidewind A, Trost C, Cavalie A et al. Expression of CaT-like, A Novel Calcium-Selective Channel, Correlates With the Malignancy of Prostate Cancer, The Journal of Biological Chemistry, Jun. 2001, pp. 19461-19468, vol. 276, No. 22, The American Society for Biochemistry and Molecular Biology.

Niemeyer BA, Bergs C, Wissenbach U, Flockerzi V, Trost C. Competitive Regulation of CaT-Like Mediated Ca2+ Entry by Protein Kinase C and Calmodulin, Proceedings of the National Academy of Sciences of the United States of America, Mar. 2001, pp. 3600-3605, vol. 98, No. 6.

Laniado ME, Fraser SP, Djamgoz MB. Voltage-Gated K(+) Channel Activity in Human Prostate Cancer Cell Lines of Markedly Different Metastatic Potential: Distinguishing Characteristics of PC-3 and LNCaP cells, The Prostate, 2001, pp. 262-274, vol. 46, No. 4, Wiley-Liss, Inc.

Shuba YM, Prevarskaya N, Lemonnier L, Van Coppenolle F, Kostyuk PG, Mauroy B et al. Volume-Regulated Chloride Conductance in the LNCaP Human Prostate Cancer Cell Line, American Journal of Physiology Cell Physiology, Oct. 2000, pp. C1144-C1154, vol. 279, No. 4, The American Physiological Society.

Fraser SP, Grimes JA, Djamgoz MB. Effects of Voltage-Gated Ion Channel Modulators on Rat Prostatic Cancer Cell Proliferation: Comparison of Strongly and Weakly Metastatic Cell Lines, The Prostate, 2000, pp. 61-76, vol. 44, No. 1, Wiley-Liss, Inc.

Rane SG. The Growth Regulatory Fibroblast IK Channel is the Prominent Electrophysiological Feature of Rat Prostatic Cancer Cells, Biochemical and Biophysical Research Communications, Mar. 2000, pp. 457-463, vol. 269, No. 2, Academic Press.

Skryma R, Van Coppenolle F, Dufy-Barbe L, Dufy B, Prevarskaya N. Characterization of Ca(2+)-Inhibited Potassium Channels in the LNCaP Human Prostate Cancer Cell Line, Receptors and Channels, 1999, pp. 241-253, vol. 6, No. 4, Harwood Academic Publishers, Malaysia.

Diss JK, Stewart D, Fraser SP, Black JA, Dib-Hajj S, Waxman SG et al. Expression of Skeletal Muscle-Type Voltage-Gated Na+ Channel in Rat and Human Prostate Cancer Cell Lines, FEBS Letters, May 1998, pp. 5-10, vol. 427, No. 1, Elsevier on Behalf of the Federation of European Biochemical Sciences.

Grimes JA, Djamgoz MB. Electrophysiological Characterization of Voltage-Gated Na+ Current Expressed in the Highly Metastatic Mat-LyLu Cell Line of Rat Prostate Cancer, Journal of Cellular Physiology, Apr. 1998, pp. 50-58, vol. 175, No. 1, Wiley-Liss, Inc.

Skryma RN, Prevarskaya NB, Dufy-Barbe L, Odessa MF, Audin J, Dufy B. Potassium conductance in the Androgen-Sensitive Prostate Cancer Cell Line, LNCaP: Involvement in Cell Proliferation, The Prostate, 1997, pp. 112-122, vol. 33, No. 2, Wiley-Liss, Inc.

Laniado ME, Lalani EN, Fraser SP, Grimes JA, Bhangal G, Djamgoz MB et al. Expression and Functional Analysis of Voltage-Activated Na+ channels in Human Prostate Cancer Cell Lines and Their Contribution to Invasion in Vitro, The American Journal of Pathology, Apr. 1997, pp. 1213-1221, vol. 150, No. 4, American Society for Investigative Pathology.

Grimes JA, Fraser SP, Stephens GJ, Downing JE, Laniado ME, Foster CS et al. Differential Expression of Voltage-Activated Na+ currents in Two Prostatic Tumour Cell Lines: Contribution to Invasiveness in Vitro, FEBS Letters, Aug. 1995, pp. 290-294, vol. 369, No. 2-3, Elsevier on Behalf of the Federation of European Biochemical Societies.

Wykoff CC, Beasley N, Watson PH, Campo L, Chia SK, English R et al. Expression of the Hypoxia-Inducible and Tumor-Associated Carbonic Anhydrases in Ductal Carcinoma in Situ of the Breast, The American Journal of Pathology, Mar. 2001, pp. 1011-1019, vol. 158, No. 3, American Society for Investigative Pathology.

Stemmer-Rachamimov AO, Wiederhold T, Nielsen GP, James M, Pinney-Michalowski D, Roy JE et al. NHE-RF, A Merlin-Interacting Protein, is Primarily Expressed in Luminal Epithelia, Proliferative Endometrium, and Estrogen Receptor-Positive Breast Carcinomas, The American Journal of Pathology, Jan. 2001, pp. 57-62, vol. 158, No. 1, American Society for Investigative Pathology.

Klimatcheva E, Wonderlin WF. An ATP-Sensitive K(+) Current That Regulates Progression Through Early G1 Phase of the Cell Cycle in MCF-7 Human Breast Cancer Cells, The Journal of Membrane Biology, Sep. 1999, pp. 35-46, vol. 171, No. 1, Spinger.

Liu MP, Handschumacher RE. Tamoxifen Induces Na+-Dependent Uridine Transport and Dome Formation in a Human Breast Tumor Cell Line, The Cancer Journal from Scientific American, Aug. 1995, pp. 210-214, vol. 1, No. 3.

Shen MR, Droogmans G, Eggermont J, Voets T, Ellory JC, Nilius B. Differential expression of Volume-Regulated Anion Channels During Cell Cycle Progression of Human Cervical Cancer Cells, The Journal of Physiology, Dec. 2000, pp. 385-394, vol. 529, Pt 2, The Physiological Society.

Shen MR, Chou CY, Ellory JC. Volume-Sensitive KCl cotransport Associated With Human Cervical Carcinogenesis, Pflügers Archibe European Journal of Physiology, Sep. 2000, pp. 751-760, vol. 440, No. 5, Springer.

Chou CY, Shen MR, Wu SN. Volume-sensitive Chloride Channels Associated With Human Cervical Carcinogenesis, Cancer Research, Dec. 1995, pp. 6077-6083, vol. 55, No. 24, Official Journal of the American Association for Cancer Research.

Allen DH, Lepple-Wienhues A, Cahalan MD. Ion Channel Phenotype of Melanoma Cell Lines, The Journal of Membrane Biology, 1997, pp. 27-34, vol. 155, No. 1, Springer.

Nilius B, Wohlrab W. Potassium Channels and Regulation of Proliferation of Human Melanoma Cells, The Journal of Physiology, 1992, pp. 537-548, vol. 445, Cambridge University Press.

Nilius B, Bohm T, Wohlrab W. Properties of a Potassium-Selective Ion Channel in Human Melanoma Cells, Pflügers Archive European Journal of Physiology, Nov. 1990, pp. 269-277, vol. 417, No. 3, Springer International.

Cartman ML, Morris JA, Huddart H, Staff WG. Electrolyte Homeostasis in Urothelial Neoplasia: The Effects of Amiloride, British Journal of Urology, May 1995, pp. 599-603. Volume 75, No. 5, Blackwell Science, Ltd.

Chien JL, Warren JR. Free Calcium and Calmodulin Levels in Acinar Carcinoma and Normal Acinar Cells of Rat Pancreas, International Journal of Pancreatology, Mar. 1988, pp. 113-127, vol. 3, No. 2-3, Elsevier.

Kim JA, Kang YS, Jung MW, Lee SH, Lee YS. Involvement of Ca2+ Influx in the Mechanism of Tamoxifen-Induced Apoptosis in HepG2 Human Hepatoblastoma Cells, Cancer Letters, Dec. 1999, pp. 115-123, vol. 147, No. 1-2, Elsevier.

Gutierrez AA, Arias JM, Garcia L, Mas-Oliva J, Guerrero-Hernandez A. Activation of a Ca2+-Permeable Cation Channel by Two Different Inducers of Apoptosis in a Human Prostatic Cancer Cell Line, The Journal of Physiology, May 1999, pp. 95-107, vol. 517, Pt 1, The Physiological Society.

Tapia-Vieyra JV, Mas-Oliva J. Apoptosis and Cell Death Channels in Prostate Cancer, Archives of Medical Research, 2001, pp. 175-185, vol. 32, No. 3, Elsevier Science, Inc.

Elble RC, Pauli BU. Tumor Suppression by a Proapoptotic Calcium-Activated Chloride Channel in Mammary Epithelium, The Journal of Biological Chemistry, Nov. 2001, pp. 40510-40517, vol. 276, No. 44, The American Society for Biochemistry and Molecular Biology.

Kim JA, Kang YS, Lee YS. Involvement of K(+)-Cl(−)-cotransport in the Apoptosis Induced by N-Ethylmaleimide in HepG2 Human Hepatoblastoma Cells, European Journal of Pharmacology, Apr. 2001, pp. 1-5, vol. 418, Nos. 1-2, Elsevier.

Loewenstein WR. Junctional Intercellular Communication and the Control of Growth, Biochimica et Biophysica Acta , Feb. 1979, pp. 1-65, vol. 560, No. 1, Elsevier/North-Holland.

Loewenstein WR. Junctional Cell-To-Cell Communication and Growth Control, Annals of the New York Academy of Sciences, 1980, pp. 39-45, vol. 339, The New York Academy of Sciences, New York, USA.

Pauli BU, Weinstein RS. Structure of Gap Junctions in Cultures of Normal and Neoplastic Bladder Epithelial Cells, Experientia, 1981, pp. 248-250. vol. 37, No. 3, Birkhaüser Verlag.

Slaughter DP, Southwick HW, Smejkal W. "Field Cancerization" in Oral Squamous Epithelium: Clinical Implications of Multicentric Origin, Cancer, A Journal of American Cancer, Jul. 1953, pp. 963-968, vol. 6, No. 4, J.B. Lippincott Company, Philadelphia, PA, USA.

Bernstein JM, Gorfien J, Noble B, Yankaskas JR. Nasal polyposis: Immunohistochemistry and Bioelectrical Findings (A Hypothesis for the Development of Nasal Polyps), The Journal of Allergy and Clinical Immunology, Feb. 1997, pp. 165-175, vol. 99, No. 2, Mosby.

Bernstein JM, Yankaskas JR. Increased Ion transport in Cultured Nasal Polyp Epithelial Cells, Archives of Otolaryngology of Head & Neck Surgery, Sep. 1994, pp. 993-996, vol. 120, No. 9, American Medical Association.

Marina AA, Iliev IG, Schwalke MA, Gonzalez E, Marler KC, Flanagan CA. Association Between Cell Membrane Potential and Breast Cancer, Tumour Biology, 1994, pp. 82-89, vol. 15, No. 2.

Morimoto T, Kinouchi Y, Iritani T, Kimura S, Konishi Y, Mitsuyama N et al. Measurement of the Electrical Bio-Impedance of Breast Tumors, European Surgical Research, Apr. 1990, pp. 86-92, vol. 22, No. 2, S. Karger Medical and Scientific Publishers.

Thurnherr N, Deschner EE, Stonehill EH, Lipkin M. Induction of Adenocarcinomas of the Colon in Mice by Weekly Injections of 1,2-dimethylhydrazine, Cancer Research, May 1973, pp. 940-945, vol. 33, No. 5.

Hebestreit A, Kersting U, Basler B, Jeschke R, Hebestreit H. Exercise Inhibits Epithelial Sodium Channels in Patients With Cystic Fibrosis, American Journal of Respiratory and Critical Care Medicine, Jul. 2001, pp. 443-446, vol. 164, No. 3.

Orlando RC, Powell DW, Croom RD, Berschneider HM, Boucher RC, Knowles MR. Colonic and Esophageal Transepithelial Potential Difference in Cystic Fibrosis, Gastroenterology, Apr. 1989, pp. 1041-1048, vol. 96, No. 4, American Gastroentrological Association.

Hay JG, Geddes DM. Transepithelial Potential Difference in Cystic Fibrosis, The Journal of the British Thoracic Society, Jul. 1985, pp. 493-496, vol. 40, No. 7, British Medical Association, London, England.

Knowles M, Gatzy J, Boucher R. Increased Bioelectric Potential Difference Across Respiratory Epithelia in Cystic Fibrosis, New England Journal of Medicine, Dec. 1981, pp. 1489-1495, vol. 305, No. 25, Massachusets Medical Society.

Oksiejczuk E, Figaszewski Z. Electrokinetic Potential of Lung Cancer Cells, Rocziniki Akademii Medycznej Bialymstoku, 1997, pp. 340-354, vol. 42, Supplement 1.

Marina AA, Morris DM, Schwalke MA, Iliev IG, Rogers S. Electrical Potential Measurements in Human Breast Cancer and Benign Lesions, Tumour Biology, Jan. 1994, pp. 147-152, vol. 15, No. 3, S. Karger.

Broggi G, Franzini A. Value of Serial Stereotactic Biopsies and Impedance Monitoring in the Treatment of Deep Brain Tumours, Journal of Neurology Neurosurgery and Psychiatry, May 1981, pp. 397-401, vol. 44, No. 5, British Medical Association, London, England.

Fukuda M, Shimizu K, Okamoto N, Arimura T, Ohta T, Yamaguchi S et al. Prospective Evaluation of Skin Surface Electropotentials in Japanese Patients With Suspicious Breast Lesions, Japanese Journal of Cancer Research, Oct. 1996, pp. 1092-1096, vol. 87, No. 10, Elsevier Science, Ltd., Ireland and Business Center for Academic Societies. Japan.

Chauveau N, Hamzaoui L, Rochaix P, Rigaud B, Voigt JJ, Morucci JP. Ex Vivo Discrimination Between Normal and Pathological Tissues in Human Breast Surgical Biopsies Using Bioimpedance Spectroscopy, Annals of the New York Academy of Sciences, 1999, pp. 42-50, vol. 873, The New York Academy of Science, New York, NY, USA.

dA Silva JE, De Sa JP, Jossinet J. Classification of Breast Tissue by Electrical Impedance Spectroscopy, Medical and Biological Engineering & Computing. Jan. 2000, pp. 26-30, vol. 38, No. 1.

Jossinet J. Variability of Impedivity in Normal and Pathological Breast Tissue, Medical & Biological Engineering & Computing, Sep. 1996, pp. 246-350, vol. 34, No. 5.

Jossinet J. The Impedivity of Freshly Excised Human Breast Tissue, Physiological Measurement, Feb. 1998, pp. 61-75, vol. 19, No. 1, Institute of Physics Publishing.

Jossinet J, Schmitt M. A Review of Parameters for the Bioelectrical Characterization of Breast Tissue, Annals of the New York Academy of Sciences, 1999, pp. 30-41, vol. 873, The New York Academy of Sciences, New York, NY.

Brown BH, Tidy JA, Boston K, Blackett AD, Smallwood RH, Sharp F. Relation Between Tissue Structure and Imposed Electrical Current Flow in Cervical Neoplasia, The Lancet, Mar. 2000, pp. 892-895, vol. 355, No. 9207, The Lancet Publishing Group, Ltd., Elsevier Sciences Ltd.

Cherepenin V, Karpov A, Korjenevsky A, Kornienko V, Mazaletskaya A, Mazourov D et al. A 3D Electrical Impedance Tomography (EIT) System for Breast Cancer Detection, Physiological Measurement, Feb. 2001, pp. 9-18, vol. 22, No. 1, Institute of Physics Publishing.

Gonzalez-Correa CA, Brown BH, Smallwood RH, Kalia N, Stoddard CJ, Stephenson TJ et al. Virtual Biopsies in Barrett's Esophagus Using an Impedance Probe, Annals of New York Academy of Sciences, 1999, pp. 313-321, vol. 873, The New York Academy of Sciences, New York, NY, USA.

Gonzalez-Correa CA, Brown BH, Smallwood RH, Kalia N, Stoddard CJ, Stephenson TJ et al. Assessing the Conditions for in Vivo Electrical Virtual Biopsies in Barrett's Oesophagus, Medical & Biological Engineering & Computing, Jul. 2000, pp. 373-376, vol. 38, No. 4.

Gorecki J, Dolan EJ, Tasker RR, Kucharczyk W. Correlation of CT and MR With Impedance Monitoring and Histopathology in Stereotactic Biopsies, The Canadian Journal of Neurological Sciences, May 1990, pp. 184-189, vol. 17, No. 2.

Kimura S, Morimoto T, Uyama T, Monden Y, Kinouchi Y, Iritani T. Application of Electrical Impedance Analysis for Diagnosis of a Pulmonary Mass, Chest, 1994, pp. 1679-1682, vol. 105, No. 6, Official Publication of American College of Chest Physicians.

Malich A, Fritsch T, Anderson R, Boehm T, Freesmeyer MG, Fleck M et al. Electrical Impedance Scanning for Classifying Suspicious Breast Lesions: First Results, European Radiology, 2000, pp. 1555-1561, vol. 10, No. 10, Springer-Verlag.

Malich A, Boehm T, Facius M, Freesmeyer MG, Fleck M, Anderson R et al. Differentiation of Mammographically Suspicious Lesions: Evaluation of Breast Ultrasound, MRI Mammography and Electrical Impedance Scanning as Adjunctive Technologies in Breast Cancer Detection, Clinical Radiology, Apr. 2001, pp. 278-283, vol. 56, No. 4, WB Saunders Company LTD.

Malich A, Fritsch T, Mauch C, Boehm T, Freesmeyer M, Fleck M et al. Electrical impedance Scanning: A New Technique in the Diagnosis of Lymph Nodes in Which Malignancy is Suspected on Ultrasound, British Journal of Radiology, 2001, pp. 42-47, vol. 74, No. 877.

Morimoto T, Kimura S, Konishi Y, Komaki K, Uyama T, Monden Y et al. A Study of the Electrical Bio-Impedance of Tumors, Journal of Investigative Surgeries, 1993, pp. 25-32, vol. 6, No. 1, Taylor & Francis, New York, USA.

Ohmine Y, Morimoto T, Kinouchi Y, Iritani T, Takeuchi M, Monden Y. Noninvasive Measurement of the Electrical Bioimpedance of Breast Tumors, Anticancer Research, Jun. 2000, pp. 1941-1946, vol. 20, No. 3B.

Piperno G, Frei EH, Moshitzky M. Breast Cancer Screening by Impedance Measurements, Frontiers in Medical and Biological Engineering, 1990, pp. 111-117, vol. 2, No. 2.

Poupa V, Setka J, Vrana J. [Diagnosis of Malignant Diseases of the Mucosa of the Gastrointestinal Tract by Impedance Measurement Using the DIACA Apparatus], Rozhledy Chirurgii, 1986, pp. 316-321, vol. 65, No. 5.

Setka J, Vrana J. [Impedance of the Recto-Sigmoidal Mucosa Measured by Endoscopy in the Diagnosis of Rectal Neoplasms], Archives Francaises des Maladies de L'Appareil Digestif, 1969, pp. 477-482, vol. 58, No. 7, Masson & Cie, Paris, France.

Setka J, Vrana J. [Impedance in the Endoscopy of Rectal Neoplasms], Sb Ornik Lekarsky, 1970, pp. 89-93, vol. 72, No. 4.

Brown BH. Impedance Tomography and Spectroscopy: What can and what will we see? in: Sverre Grimnes, Ørjan G.Martinsen, Heidi Bruvoll, editors. Proceedings XI International Conference on Electrical Bio-Impedance. Oslo, Norway, University of Oslo, 2001: 9-13.

Thompson SM, Suzuki Y, Schultz SG. The Electrophysiology of Rabbit Descending Colon. I. Instantaneous Transepithelial Current-Voltage Relations and the Current-Voltage Relations of the Na-Entry Mechanism, Journal of Membrane Biology, 1982, pp. 41-45, vol. 66, No. 1, Springer-Verlag, New York New York, USA.

Brasitus TA, Dudeja PK, Foster ES. 1,2-Dimethylhydrazine-induced Alterations in Na+-H+ Exchange in Rat Colonic Brush-Border Membrane Vesicles, Biochimica et Biophysica Acta, Mar. 1988, pp. 483-488, vol. 938, No. 3, Elsevier.

Davies RJ, Asbun H, Thompson SM, Goller DA, Sandle GI. Uncoupling of Sodium Chloride Transport in Premalignant Mouse Colon, Gastroenterology, Jun. 1990, pp. 1502-1508, vol. 98, No. 6, American Gastroenterological Association.

Fraser GM, Portnoy M, Bleich M, Ecke D, Niv Y, Greger R et al. Characterization of Sodium and Chloride Conductances in Preneoplastic and Neoplastic Murine Colonocytes, Pflugers Archive European Journal of Physiology, Nov. 1997, pp. 801-808, vol. 434, No. 6, Springer.

Schwan, H.P., Electrical Properties of Tissue and Cell Suspensions in: "Advances in Biological and Medical Physics," J.H. Lawrence and C.A. Tobias, Eds. vol. V, 1957, p. 147, Aladdin Press, Inc., New York.

Foster, Kenneth R., Bioimpedance as Medical Technology: What Does it Take to Succeed; University of Pennsylvania, Philadelphia, PA.

Foster KR, Schwan HP. Dielectric Properties of Tissues and Biological Materials: A Critical Review. Critical Reviews in Biomedical Engineering, 1989, pp. 25-104 vol. 17, Issue 1, CRC Press, England.

Emtestam L, Ollmar S. Electrical Impedance Index in Human Skin: Measurements After Occlusion, in 5 Anatomical Regions and in Mild Irritant Contact Dermatitis. Contact Dermatitis Environmental and Occupational Dermatitis, Feb. 1993, pp. 104-108, vol. 28, No. 2, RJG Rycroft, London, England.

Ollmar S, Eek A, Sundstrom F, Emtestam L. Electrical Impedance for Estimation of Irritation in Oral Mucosa and Skin. Medical Progress Technology, Feb. 1995, pp. 29-37, vol. 21. No. 1, Kluwer Academic Publishers.

Ollmar S, Nyren M, Nicander I, Emtestam L. Electrical Impedance Compared With Other Non-Invasive Bioengineering Techniques and Visual Scoring for Detection of Irritation in Human Skin, British Journal of Dermatology, Jan. 1994, pp. 29-36, vol. 130, No. 1, Blackwell Scientific Publications.

Nicander I, Ollmar S, Rozell BL, Eek A, Emtestam L. Electrical Impedance Measureed to Five Skin Depths in Mild Irritant Dermatitis Induced by Sodium Lauryl Sulphate, British Journal of Dermatology, May 1995, pp. 718-724, vol. 132, No. 5, Blackwell Scientific Publications.

Kristt D, Winston GJ, Mellov MM, Veltman V, Koren R. Patterns of Proliferative Changes in Crypts Bordering Colonic Tumors: Zonal Histology and Cell Cycle Marker Expression. Pathology Oncology Research, 1999; pp. 297-303, vol. 5, No. 4.

Lackermeier AH, McAdams ET, Moss GP, Woolfson AD. In Vivo Ac Impedance Spectroscopy of Human Skin. Theory and Problems in Monitoring of Passive Percutaneous Drug Delivery. Annals of the New York Academy of Sciences, 1999, pp. 197-213, vol. 873.

Cuzick J, Holland R, Barth V, Davies R, Faupel M, Fentiman I et al. Electropotential Measurements as a New Diagnostic Modality for Breast Cancer. The Lancet, Aug. 1998, pp. 359-363, vol. 352, No. 9125.

Faupel M, Vanel D, Barth V, Davies R, Fentiman IS, Holland R et al. Electropotential Evaluation as a New Technique for Diagnosing Breast Lesions. European Journal of Radiology, Jan. 1997, pp. 33-38. Volume 24, No. 1, Elsevier.

Hülser DF, Frank W. Stimulation of Embryonic Rat Cell in Culture by a Protein Fraction Isolated From Fetal Calf Serum, Publishing House of the Periodical for Nature Research, Jul. 1971, pp. 1045-1048, vol. 26b, No. 7.

Moolenaar WH, De Laat SW, Van Der Saag PT. Serum Triggers a Sequence of Rapid Ionic Conductance Changes in Quiescent Neuroblastoma Cells, Nature, Jun. 14, 1979, pp. 721-723, vol. 279, No. 5714.

Reuss L, Cassel D, Rothenberg P, Whiteley P, Mancuso D, Glaser L. Mitogens and Ion Fluxes. In: Mandel LJ, Benos DJ, Editors. The Role of Membranes in Cell Growth and Differentiation, Academic Press Inc., Hartcourt Brace Jovanovich, 1986, pp. 3-54, vol. 27, Orlando, Fla.

Moolenaar WH, De Laat SW, Mummery CL, Van Der Saag PT. Na+/H+ Exchange in the Action of Growth Factors. In: Boynton AL, McKeehan WL, Whitfield JF, editors. Ions, Cell Proliferation and Cancer, Academic Press, Inc., 1982, pp. 151-162, New York.

Rothenberg P, Reuss L, Glaser L. Serum and Epidermal Growth Factor Transiently Depolarize Quiescent BSC-1 Epithelial Cells, Proceedings of the National Academy of Sciences of The United States of America, Dec. 1982, pp. 7783-7787, vol. 79, No. 24.

Schultz SG. Homocellular Regulatory Mechanisms in Sodium-Transporting Epithelia: Avoidance of Extinction by "Flush-Through", American Journal of Physiology, Dec. 1981, pp. F579-F590, vol. 241, No. 6, The American Physiological Society.

Boonstra J, Moolenaar WH, Harrison PH, Moed P, Van Der Saag PT, De Laat SW. Ionic Responses and Growth Stimulation Induced by Nerve Growth Factor and Epidermal Growth Factor in Rat Pheochromocytoma (PC12) cells, The Journal of Cell Biology, Jul. 1983, pp. 92-98, vol. 97, No. 1, The Rockefeller University Press.

Redmann K, Walliser S. Different Changes in Transmembrane Potential of Cultured Cells After Ouabain-Inhibited Active Na+/K+-Transport. Archiv Fur Geschwulstforsch, 1981; pp. 96-102. vol. 51, No. 1, Volk and Gesundheit, Berlin.

Prat AG, Cunningham CC, Jackson GR, Jr., Borkan SC, Wang Y, Ausiello DA et al. Actin Filament Organization is Required for Proper Camp-Dependent Activation of CFTR., American Journal of Physiology, Dec. 1999, pp. C1160-C1169 vol. 277, No. 6 Part 1, The American Physiology Society.

Rouzaire-Dubois B, Milandri JB, Bostel S, Dubois JM. Control of Cell Proliferation by Cell Volume Alterations in Rat C6 Glioma Cells. Pflugers Archiv European Journal of Physiology, Oct. 2000, vol. 440, No. 6, Springer.

Ernst M, Adam G. Regulation of Passive Potassium Transport of Normal and Transformed 3T3 Mouse Cell Cultures by External Calcium Concentration and Temperature. Journal of Member Biology, 1981; pp. 155-172, vol. 61, No. 3, Springer-Verlag New York Inc.

Diserbo M, Fatome M, Verdetti J. Activation of Large Conductance Ca(2+)-Activated K+Channels in N1E-115 Neuroblastoma Cells by Platelet-Activating Factor. Biochemical and Biophysical Research Community, Jan. 1996, pp. 745-749, vol. 218, No. 3, Academic Press.

Rane SG. A Ca2(+)-Activated K+ Current in Ras-Transformed Fibroblasts is Absent From Nontransformed Cells, American Journal of Physiology, Jan. 1991, pp. C104-C112, vol. 260, No. 1, Part 1, The American Physiological Society.

Sachs HG, Stambrook PJ, Ebert JD. Changes in Membrane Potential During the Cell Cycle, Experimental Cell Research, Feb. 1974, pp. 362-366, vol. 83, No. 2, Academic Press, New York and London.

Kiefer H, Blume AJ, Kaback HR. Membrane Potential Changes During Mitogenic Stimulation of Mouse Spleen Lymphocytes, Proceedings of the National Academy of Sciences, of the United States of America, Apr. 1980, pp. 2200-2204, vol. 77, No. 4.

Moolenaar WH, Mummery CL, Van Der Saag PT, De Laat SW. Rapid Ionic Events and the Initiation of Growth in Serum-Stimulated Neuroblastoma Cells, Cell Mar. 1981, pp. 789-798, vol. 23, No. 3.

Chapman LM, Wondergem R. Transmembrane Potential and Intracellular Potassium Ion Activity in Fetal and Maternal Liver, Journal of Cellular Physiology, Oct. 1984, pp. 7-12, vol. 121, No. 1, Alan R. Liss, Inc.

Decoursey TE, Cherny VV. Voltage-Activated Proton Currents in Human THP-1 Monocytes, The Journal of Membrane Biology, Jul. 1996, pp. 131-140, vol. 152, No. 2, Springer.

Kapural L, Fein A. Changes in the Expression of Voltage-Gated K+ Currents During Development of Human Megakaryocytic Cells, Biochimica et Biophysica Acta 1997, pp. 319-328; vol. 1326, No. 2, Elsevier, USA.

Wieland SJ, Chou RH, Chen TA. Elevation of a Potassium Current in Differentiating Human Leukemic (HI-60) Cells, Journal of Cell Physiology, Aug. 1987, pp. 371-375, vol. 132, No. 2, Alan R. Liss, Inc.

Simonneau M, Distasi C, Tauc L, Poujeoi C. Development of Ionic Channels During Mouse Neuronal Differentiation, Journal de Physiologie, 1985, pp. 312-332, vol. 80, No. 2, Masson, Paris, France.

Veselovskii NS, Fomina AF. [Sodium and Calcium Channels of the Somatic Membrane of Neuroblastoma Cells During Artificially Induced Differentiation]. Neirofiziologiia 1986; pp. 207-214, vol. 18, No. 2.

Vyklicky L, Jr., Michl J, Vlachova V, Vyklicky L, Vyskocil F. Ionic Currents in Neuroblastoma Clone E-7 Cells, Neuroscience Letters, 1985, pp. 197-201, vol. 55, No. 2, Elsevier Scientific Publishers, Ireland.

Felber SM, Brand MD. Concanavalin A Causes an Increase in Sodium Permeability and Intracellular Sodium Content of Pig Lymphocytes, The Biochemical Journal, Mar. 1983, pp. 893-897, vol. 210, No. 3, The Biochemical Society, London.

O'Donnell ME, Villereal ML. Membrane Potential and Sodium Flux in Neuroblastoma X Glioma Hybrid Cells: Effects of Amiloride and Serum, Journal of Cellular Physiology, Dec. 1982, pp. 405-412, vol. 113, No. 3, Alan R. Liss, Inc.

Leffert HL, Koch KS. Ionic Events at the Membrane Initiate Rat Liver Regeneration. Ann The New York Academy of Sciences, 1980, pp. 201-215, vol. 339, New York, USA.

Villereal ML. Sodium Fluxes in Human Fibroblasts: Effect of Serum, Ca+2, and Amiloride. Journal of Cellular Physiology, Jun. 1981, pp. 359-369, vol. 107, No. 3, Alan R. Liss, Inc.

Fehlmann M, Canivet B, Freychet P. Epidermal Growth Factor Stimulates Monovalent Cation Transport in Isolated Rat Hepatocytes, Biochemical and Biophysical Research Communications, May 1981, pp. 254-260, vol. 100, No. 1, Academic Press Inc.

Moolenaar WH, Tsien RY, Van Der Saag PT, De Laat SW. Na+/H+ Exchange and Cytoplasmic Ph in the Action of Growth Factors in Human Fibroblasts. Nature, International Weekly Journal of Science, Aug. 1983, pp. 645-648, vol. 304, No. 5927, MacMillan Journals, Ltd.

Paris S, Pouyssegur J. Biochemical Characterization of the Amiloride-Sensitive Na+/H+ Antiport in Chinese Hamster Lung Fibroblasts, The Journal of Biological Chemistry, Mar. 1983, pp. 3503-3508, vol. 258, No. 6, The American Society of Biological Chemists, Inc., USA.

Paris S, Pouyssegur J. Growth Factors Activate the Na+/H+ Antiporter in Quiescent Fibroblasts by Increasing its Affinity for Intracellular H+, The Journal of Biological Chemistry, Sep. 1984, pp. 10989-10994, vol. 259, No. 17, The American Society of Biological Chemists, Inc., USA.

Pouyssegur J, Chambard JC, Franchi A, Paris S, Obberghen-Schilling E. Growth Factor Activation of an Amiloride-Sensitive Na+/H+ Exchange System in Quiescent Fibroblasts: Coupling to Ribosomal Protein S6 Phosphorylation, Proceedings of the National Academy of Sciences of the United States of America, Jul. 1982, pp. 3935-3939, vol. 79, No. 13, National Academy of Sciences, USA.

Pouyssegur J, Sardet C, Franchi A, L'Allemain G, Paris S. A Specific Mutation Abolishing Na+/H+ Antiport Activity in Hamster Fibroblasts Precludes Growth At Neutral and Acidic Ph., Proceedings of the National Academy of Sciences of the United States of America, Aug. 1984, pp. 4833-4837, vol. 81, No. 15, National Academy of Sciences, USA.

Moolenaar WH, Tertoolen LG, De Laat SW. The Regulation of Cytoplasmic Ph in Human Fibroblasts, The Journal of Biological Chemistry. Jun. 1984, pp. 7563-7569, vol. 259, No. 12, The American Society of Biological Chemists, Inc., USA.

Deutsch C, Price M. Role of Extracellular Na and K in Lymphocyte Activation, Journal of Cellular Physiology, Oct. 1982, pp. 73-79, vol. 113, No. 1, Alan R. Liss, Inc.

Saqr HE, Guan Z, Yates AJ, Stokes BT. Mechanisms Through Which PDGF Alters Intracellular Calcium Levels in U-1242 MG Human Glioma Cells, Neurochemistry International, Dec. 1999, pp. 411-422, vol. 35, No. 6, Elsevier Science Ltd.

Chen CF, Corbley MJ, Roberts TM, Hess P. Voltage-Sensitive Calcium Channels in Normal and Transformed 3T3 Fibroblasts, Science, Feb. 1988, pp. 1024-1026, vol. 239, No. 4843.

Owen NE, Villereal ML. Role of Ca2+ in Serum-Stimulated Na+ Influx in Normal and Transformed Cells, American Journal of Physiology, Mar. 1985, pp. C288-C295, vol. 248, No. 3 Pt 1, The American Physiological Society.

Macara IG. Oncogenes, ions, and Phospholipids, American Journal of Physiology, Jan. 1985, pp. C3-11, vol. 248, No. 1 Pt 1, The American Physiological Society.

Cameron IL, Smith NK, Pool TB, Sparks RL. Intracellular Concentration of Sodium and Other Elements as Related to Mitogenesis and Oncogenesis in Vivo, Cancer Research, May 1980, pp. 1493-1500, vol. 40, No. 5.

Goller DA, Weidema WF, Davies RJ. Transmural Electrical Potential Difference as an Early Marker in Colon Cancer. Archives of Surgery, Mar. 1986, pp. 345-350, vol. 121, No. 3, The American Medical Association, USA.

Davies RJ, Weidema WF, Sandle GI, Palmer L, Deschner EE, Decosse JJ. Sodium Transport in a Mouse Model of Colonic Carcinogenesis, Cancer Research, Sep. 1987, pp. 4646-4650, vol. 47, No. 17.

Davies RJ, Juncosa RD, Kaplan D, Pempinello C, Asbun H, Pilch YH. Colonic Epithelial Impedance Analysis in a Murine Model of Large-Bowel Cancer, Archives of Surgery, Nov. 1986, pp. 1253-1258, vol. 121, No. 11, The American Medical Association, USA.

Davies RJ, Joseph R, Kaplan D, Juncosa RD, Pempinello C, Asbun H et al. Epithelial Impedance Analysis in Experimentally Induced Colon Cancer, Biophysical Journal, Nov. 1987, pp. 783-790, vol. 52, No. 5, The Biophysical Society by the Rockefeller University Press, USA.

Davies RJ, Joseph R, Asbun H, Sedwitz M. Detection of the Cancer-Prone Colon, Using Transepithelial Impedance Analysis, Archives of Surgery, Apr. 1989, pp. 480-484, vol. 124, No. 4, The American Medical Association, USA.

Schaefer H, Schanne O. Membranpotentiale Von Einzelzellen in Gewebekulturen, Naturwissenschaften 1956, p. 445, vol. 43, Springer-Verlag.

Tokuoka S, Morioka H. The Membrane Potential of the Human Cancer and Related Cells, "GANN" The Japanese Journal of Cancer Research, Gann, 1957, pp. 353-354, vol. 48, The Japanese Cancer Association and the Japanese Foundation for Cancer Research, Nishi-Sugamo, Toshima-ku, Tokyo, Japan.

Balitsky KP, Shuba EP. Resting Potential of Malignant Cells, ACTA, Eighth International Cancer Congress, 1964, pp. 1391-1393, vol. 20, No. 67.

Cone CD, Jr. Unified Theory on the Basic Mechanism of Normal Mitotic Control and Oncogenesis, Journal of Theoretical Biology, Jan. 1971, pp. 151-181, vol. 30, No. 1, Academic Press.

Cone CD, Jr., Cone CM. Induction of Mitosis in Mature Neurons in Central Nervous System by Sustained Depolarization, Science, Apr. 1976, pp. 155-158, vol. 192, No. 4235.

Cone CD, Jr. The Role of the Surface Electrical Transmembrane Potential in Normal and Malignant Mitogenesis, Annals of the New York Academy of Sciences, 1974, pp. 420-435, vol. 238, The New York Academy of Sciences, USA.

Lai CN, Gallick GE, Arlinghaus RB, Becker FF. Temperature-Dependent Transmembrane Potential Changes in Cells Infected With a Temperature-Sensitive Moloney Sarcoma Virus, Journal of Cellular Physiology, Oct. 1984, pp. 139-142, vol. 121, No. 1, Alan R. Liss, Inc.

Binggeli R, Cameron IL. Cellular Potentials of Normal and Cancerous Fibroblasts and Hepatocytes, Cancer Research, Jun. 1980, pp. 1830-1835, vol. 40, No. 6.

Koch KS, Leffert HL. Growth Control of Differentiated Adult Rat Hepatocytes in Primary Culture, Annals of the New York Academy of Sciences, 1980, pp. 111-127, vol. 349, The New York Academy of Sciences, New York, USA.

Funkhouser WK, Pilch YH, Davies RJ. The Electrophysiologic Changes Associated with Premalignancy in Colon Carcinogenesis, Federation Proceedings, Mar. 1986, p. 742, vol. 45, No. 4, Federation of American Societies for Experimental Biology.

Huang Y, Rane SG. Single Channel Study of a Ca(2+)-Activated K+ Current Associated With Ras-Induced Cell Transformation, The Journal of Physiological Society, 1993, pp. 601-618, vol. 461, Cambridge University Press.

Davies RJ, Weiss A, Capko D, Brenner BM. Cell Membrane Potential in Benign and Malignant Breast Epithelial Cells. Breast Cancer Research and Treatment, 1996, p. 331, vol. 41, No. 3 Ref Type: Abstract, Kluwer Academic Publishers.

Schultz SG. Basic Principles of Membrane Transport, 1 ed. 1980, Cambridge University Press, London and New York.

Nagy IZ, Lustyik G, Nagy VZ, Zarandi B, Bertoni-Freddari C. Intracellular Na+:K+ Ratios in Human Cancer Cells As Revealed by Energy Dispersive X-Ray Microanalysis, The Journal of Cell Biology, Sep. 1981, pp. 769-777, vol. 90, No. 3, The Rockefeller University Press, USA.

Bustin SA, Li SR, Dorudi S. Expression of the Ca2+-Activated Chloride Channel Genes CLCA1 and CLCA2 is Downregulated in Human Colorectal Cancer, DNA and Cell Biology, Nov. 2001, pp. 331-338, vol. 20, No. 6, Mary Ann Liebert, Inc., London, U.K.

Broaddus RR, Wargovich MJ, Castro GA. Early stages of 1,2-dimethylhydrazine-Induced Colon Carcinogenesis Suppress Immune-Regulated Ion Transport of Mouse Distal Colon, Cancer Research, Nov. 1994, pp. 5930-5936, vol. 54, No. 22, Official Journal of the American Association for Cancer Research, USA.

Morris AP, Cunningham SA, Benos DJ, Frizzell RA. Cellular Differentiation is Required for cAMP But Not Ca(2+)-dependent Cl-Secretion in Colonic Epithelial Cells Expressing High Levels of Cystic Fibrosis Transmembrane Conductance Regulator, The Journal of Biological Chemistry, Mar. 1992, pp. 5575-5583, vol. 267, No. 8, The American Society for Biochemistry and Molecular Biology.

Champigny G, Verrier B, Lazdunski M. A Voltage, Calcium, and ATP Sensitive Non Selective Cation Channel in Human Colonic Tumor Cells, Biochemical and Biophysical Research Communications, May 1991, pp. 1196-1203, vol. 176, No. 3, Academic Press, Inc.

Hope et al., Technology review: The use of electrical impedance scanning in the detection of breast cancer, Breast Cancer Res 2004, 6;69-74.

Partial European Search Report, EP 03731268, dated Feb. 24, 2009.

Thielecke Hagen et al: Biohybrid microarrays: Impedimetric biosensors with 3D in vitro tissues for toxicological and biomedical screening Fresenius Journal of Analytical Chemistry, vol. 369, No. 1, Jan. 2001, pp. 23-29, XP002516085 ISSN: 0937-0633.

Ouadid-Ahidouch H, Roudbaraki M, Delcourt P, et.al. Am. J Physiol. Cell Physiol. Jul. 2004;287(1):C125-34.

Davies, R.J., Quinn, D.A., Davisson T.H. Breast Cancer Res. And Treat.vol. 88, (Suppl. 1) S221: 6005, 2004.

Davies, R.J., Quinn, D.A., Davisson T.H. Breast Cancer Res. And Treat.vol. 88, (Suppl. 1) S222-3: 6009, 2004.

Webster, M.A., Cardiff, R.D., and Muller, W.J. Proc. Natl. Acad. Sci. U.S.A. 1995 92:7849-7853.

Jhappan, C., Geiser, A.G., Kordon, E.C., Bagheri, D., Hennighausen, L., Roberts, A.B., Smith, G.H., and Merlino, G. Embo J. 1993 12:1835-1845. [6] Stojadinovic A, Nissan A, Gallimidi Z, et.al. J Clin Oncol Apr. 20, 2005; 23 (12):2703-15.

Stojadinovic A, Nissan A, Gallimidi Z, et.al. J Clin Oncol Apr. 20, 2005; 23(12):2703-15.

* cited by examiner

METHOD AND SYSTEM FOR DETECTING ELECTROPHYSIOLOGICAL CHANGES IN PRE-CANCEROUS AND CANCEROUS TISSUE

This application is a divisional of U.S. application Ser. No. 10/151,233, filed on May 20, 2002, the disclosure of which is hereby incorporated herein by reference.

BACKGROUND OF THE INVENTION

The present invention relates generally to the detection of abnormal or cancerous tissue and, more particularly, to the detection of changes in electrophysiological characteristics of abnormal or cancerous tissue related to the functional, structural, and topographic relationships of the tissue during the development of malignancy. These measurements may be made in the absence and/or presence of pharmacological or hormonal agents to reveal and accentuate electrophysiological characteristics indicative of abnormal or cancerous tissue.

Cancer is a leading cause of death in both men and women in the United States. Difficulty in detecting abnormal pre-cancerous or cancerous tissue before treatment options become non-viable is one reason for the high mortality rate. Detecting the presence of abnormal or cancerous tissues is difficult, in part, because such tissues are largely located deep within the body, thus requiring expensive, complex, invasive, and/or uncomfortable procedures. For this reason, the use of detection procedures is often restricted until a patient is experiencing symptoms related to the abnormal tissue. Many forms of cancers or tumors, however, require extended periods of time to attain a detectable size (and thus to produce significant symptoms or signs in the patient). It is often too late for effective treatment by the time the cancer or tumor is detected using currently available diagnostic modalities.

One proposed method for early detection of cancerous and pre-cancerous tissue includes measuring of the electrical impedance of biological tissue. For example, U.S. Pat. No. 3,949,736 discloses a low-level electric current passed through tissue, with a measurement of the voltage drop across the tissue providing an indirect indication of the overall tissue impedance. This method teaches that a change in impedance of the tissue is associated with an abnormal condition of the cells composing the tissue, indicating a tumor, carcinoma, or other abnormal biological condition. This disclosure, however, does not discuss either an increase or decrease in impedance associated with abnormal cells, nor does it specifically address tumor cells.

One disadvantage of this and similar systems is that the inherent DC electrical properties of the epithelium are not considered. Many common malignancies develop in an epithelium, often the cell layer that lines a hollow organ, such as the bowel, or in ductal structures, such as the breast or prostate. Epithelial tissue maintains a transepithelial electropotential (TEP) that may be altered by the malignancy process. Early in the malignant process, the epithelium may lose its transepithelial potential, particularly when compared to epithelium some distance away from the developing malignancy. Thus, the combination of transepithelial electropotential measurements with impedance may be more accurate in diagnosing pre-cancerous and cancerous conditions.

Another disadvantage of the above referenced system is that the frequency range is not defined. Certain information may be obtained about cells according to the range of frequencies selected. Different frequency bands may be associated with different structural or functional aspects of the tissue. See, for example, F. A. Duck, *Physical Properties of Tissues*, London: Academic Press, 2001; K. R. Foster, H. P. Schwan, Dielectric properties of tissues and biological materials: a critical review, *Crit. Rev. Biomed. Eng.*, 1989, 17(1): 25-104. For example at high frequencies, such as >1 GHz, molecular structure has a dominating effect on the relaxation characteristics of the impedance profile. Relaxation characteristics include the delay in response of a tissue to a change in the applied electric field. For example, an applied AC current results in a voltage change across the tissue which will be delayed, or phase shifted, because of the impedance characteristics of the tissue. Relaxation and dispersion characteristics of tissue vary according to the frequency of the applied signal.

At lower frequencies, such as <100 Hz, or the so called $\alpha$-dispersion range, alterations in ion transport and charge accumulations at large cell membrane interfaces dominate the relaxation characteristics of the impedance profile. In the frequency range between a few kHz and 1 MHz, or the so-called $\beta$-dispersion range, cell structure dominates the relaxation characteristics of the epithelial impedance profile. Within this range at low kHz frequencies, most of the applied current passes between the cells through the paracellular pathway and tight junctions. At higher frequencies in the $\beta$-dispersion range the current can penetrate the cell membrane and therefore passes both between and through the cells, and the current density will depend on the composition and volume of the cytoplasm and cell nucleus.

Characteristic alterations occur in the ion transport of an epithelium during the process of malignant transformation affecting the impedance characteristics of the epithelium measured at frequencies in the $\alpha$-dispersion range. Later in the malignant process, structural alterations with opening of the tight junctions and decreasing resistance of the paracellular pathways, together with changes in the composition and volume of the cell cytoplasm and nucleus, affect the impedance measured in the $\beta$-dispersion range.

Another disadvantage of the above referenced system is that the topography of altered impedance is not examined. By spacing the measuring electrodes differently, the epithelium can be probed to different depths. The depth that is measured by two surface electrodes is approximately half the distance between the electrodes. Therefore, electrodes 1 mm apart will measure the impedance of the underlying epithelium to a depth of approximately 500 microns. It is known, for example, that the thickness of bowel epithelium increases at the edge of a developing tumor to 1356±208µ compared with 716±112µ in normal bowel. D. Kristt, et al. Patterns of proliferative changes in crypts bordering colonic tumors: zonal histology and cell cycle marker expression. *Pathol. Oncol. Res* 1999; 5(4): 297-303. By comparing the measured impedance between electrodes spaced approximately 2.8 mm apart with the impedance of electrodes spaced approximately 1.4 mm apart, information about the deeper and thickened epithelium may be obtained. See, for example, L. Emtestam & S. Ollmar. Electrical impedance index in human skin: measurements after occlusion, in 5 anatomical regions and in mild irritant contact dermatitis. *Contact Dermatitis* 1993; 28(2): 104-108.

Another disadvantage of the above referenced methods is that they do not probe the specific conductive pathways that are altered during the malignant process. For example, potassium conductance is reduced in the surface epithelium of the colon early in the malignant process.

Other patents, such as U.S. Pat. Nos. 4,955,383 and 5,099,844, disclose that surface electropotential measurements may be used to diagnose cancer. Empirical measurements, however, are difficult to interpret and use in diagnosis. For example, the above referenced inventions diagnose cancer by measuring voltage differences (differentials) between one region of the breast and another and then comparing them with measurements in the opposite breast. Changes in the measured surface potential may be related to differences in the impedance characteristics of the overlying skin. This fact is ignored by the above referenced and similar inventions, resulting in a diagnostic accuracy of 72% or less. J. Cuzick et al. Electropotential measurements as a new diagnostic modality for breast cancer. *Lancet* 1998; 352(9125): 359-363; M. Faupel et al. Electropotential evaluation as a new technique for diagnosing breast lesions. *Eur. J. Radiol.* 1997; 24 (1): 33-38.

Other inventions that use AC measurement, such as U.S. Pat. No. 6,308,097, also have a lower accuracy than may be possible with a combination of DC potential measurements and AC impedance measurements. The above referenced system diagnoses cancer by only measuring decreased impedance (increased conductance) over a cancer.

Another potential source of information for the detection of abnormal tissue is the measurement of transport alterations in the mucosa. Epithelial cells line the surfaces of the body and act as a barrier to isolate the body from the outside world. Not only do epithelial cells serve to insulate the body, but they also modify the body's environment by transporting salts, nutrients, and water across the cell barrier while maintaining their own cytoplasmic environment within fairly narrow limits. One mechanism by which the epithelial layer withstands the constant battering is by continuous proliferation and replacement of the barrier. This continued cell proliferation may partly explain why more than 80% of cancers are of epithelial cell origin.

It is known that the addition of serum to quiescent fibroblasts results in rapid cell membrane depolarization. Cell membrane depolarization is an early event that may be associated with cell division. Depolarization induced by growth factors appears biphasic in some instances, but cell division may be stimulated without depolarization. Cell membrane depolarization is temporally associated with $Na^+$ influx, and the influx persists after repolarization has occurred. Although the initial $Na^+$ influx may result in depolarization, the increase in sodium transport may not cease once the cell membrane has been repolarized, possibly due to Na/K ATPase pump activation. Other studies also support that $Na^+$ transport is altered during cell activation. In addition to altered $Na^+$ transport, transport of $K^+$ and of $Cl^-$ is altered during cell proliferation.

A number of studies have demonstrated that proliferating cells are relatively depolarized when compared to those that are quiescent or non-dividing. Differentiation is associated with the expression of specific ion channels. Additional studies indicate that cell membrane depolarization occurs because of alterations in ionic fluxes, intracellular ionic composition, and transport mechanisms that are associated with cell proliferation.

Intracellular $Ca^{2+}$ ($Ca^{2+}_i$) and intracellular pH ($pH_i$) are increased by mitogen activation. Cell proliferation may be initiated following the activation of phosphatidylinositol which releases two second messengers, 1,2-diacylglycerol and inosotol-1,4,5-triphosphate, which trigger $Ca^{2+}_i$ release from internal stores. $Ca^+$ i and $pH_i$ may then alter the gating of various ion channels in the cell membrane, which are responsible for maintaining the voltage of the cell membrane. Therefore, there is the potential for interaction between other intracellular messengers, ion transport mechanisms, and cell membrane potential. Most studies have been performed in transformed and cultured cells and not in intact epithelia during the development of cancer, so that it is largely unknown how up-regulated proliferation affects cell membrane potential, transepithelial potential, epithelial impedance, and ion transport during carcinogenesis.

It was known that cancer cells are relatively depolarized compared to non-transformed cells (56-58). It has been suggested that sustained cell membrane depolarization results in continuous cellular proliferation and that malignant transformation results as a consequence of sustained depolarization and a failure of the cell to repolarize after cell division. C. D. Cone Jr., Unified theory on the basic mechanism of normal mitotic control and oncogenesis. *J. Theor. Biol.* 1971; 30(1): 151-181; C. D. Cone Jr., C. M. Cone. Induction of mitosis in mature neurons in central nervous system by sustained depolarization. *Science* 1976; 192(4235): 155-158; C. D. Cone, Jr. The role of the surface electrical transmembrane potential in normal and malignant mitogenesis. *Ann. N.Y. Acad. Sci.* 1974; 238: 420-435. A number of studies have demonstrated that cell membrane depolarization occurs during transformation and carcinogenesis. Other studies have demonstrated that a single ras-mutation may result in altered ion transport and cell membrane depolarization. Y. Huang, S. G. Rane, Single channel study of a Ca(2+)-activated $K^+$ current associated with ras induced cell transformation. *J. Physiol.* 1993; 461: 601-618. For example, there is a progressive depolarization of the colonocyte cell membrane during 1,2 dimethylhydrazine (DMH)-induced colon cancer in $CF_1$ mice. The $V_A$ (apical membrane voltage) measured with intracellular microelectrodes in histologically "normal" colonic epithelium depolarized from −74.9 mV to −61.4 mV after 6 weeks of DMH treatment and to −34 mV by 20 weeks of treatment.

While epithelial cells normally maintain their intracellular sodium concentration within a narrow range, electronmicroprobe analysis shows that cancer cells exhibit cytoplasmic sodium/potassium ratios that are three to five times greater than those found in their non-transformed ones. These observations partly explain the electrical depolarization observed in malignant or pre-malignant tissues, because of the loss of $K^+$ or $Na^+$ gradients across the cell membrane.

In addition to cell membrane depolarization, and altered intracellular ionic activity, other studies have shown that there may be a decrease in electrogenic sodium transport and activation of non-electrogenic transporters during the development of epithelial malignancies(52). These changes may occur as a consequence of altered intracellular ionic composition. Other specific ion transport alterations have been described in colon, prostate, breast, uterine cervix, melanoma, urothelium, and pancreas during proliferation, differentiation, apoptosis, and carcinogenesis.

Apoptosis or physiological cell death is down-regulated during the development of malignancy. Ion transport mechanisms affected by apoptosis include the influx of $Ca^{2+}$, non-selective $Ca^{2+}$-permeable cation channels, calcium-activated chloride channels(102), and $K^+$-$Cl^-$-cotransport. J. A. Kim et al. Involvement of Ca2+ influx in the mechanism of tamoxifen-induced apoptosis in Hep2G human hepatoblastoma cells. *Cancer Lett.* 1999; 147(1-2): 115-123; A. A. Gutierrez et al. Activation of a Ca2+-permeable cation channel by two different inducers of apoptosis in a human prostatic cancer cell line. *J. Physiol.* 1999; 517 (Pt. 1): 95-107; J. V. Tapia-Vieyra, J. Mas-Oliva. Apoptosis and cell death channels in prostate cancer. *Arch. Med. Res.* 2001; 32(3): 175-185; R. C. Elble, B. U. Pauli. Tumor Supression by a Proapoptotic Calcium-Activated Chloride Channel in Mammary Epithelium. *J. Biol. Chem.* 2001; 276(44): 40510-40517.

Loss of cell-to-cell communication occurs during carcinogenesis. This results in defective electrical coupling between cells, which is mediated via ions and small molecules through gap junctions, which in turn influences the electrical properties of epithelia.

Polyps or overtly malignant lesions may develop in a background of disordered proliferation and altered transepithelial ion transport. Experimental animal studies of large bowel cancer have demonstrated that transepithelial depolarization is an early feature of the pre-malignant state. In nasal polyp studies, the lesions had a higher transepithelial potential, but these lesions were not pre-malignant in the same sense as an adenomatous or pre-malignant colonic polyp, that are usually depolarized. Electrical depolarization has been found in biopsies of malignant breast tissue. Recently alterations in impedance have been found to be associated with the pre-malignant or cancerous state in breast and bowel.

DC electrical potential alterations have been reported to be useful to diagnose non-malignant conditions such as cystic fibrosis, cancer in animal models, human cells or isolated tissue, and in man. Differences in impedance between normal tissue and cancer have been described in animal models in vitro and have been applied to in vivo cancer diagnosis. DC potential measurements have not been combined with impedance measurements to diagnose cancer, however, because electrophysiological alterations that accompany the development of cancer are generally not fully characterized. Transepithelial depolarization is an early event during carcinogenesis, which may affect a significant region of the epithelium (a "field defect"). This depolarization is accompanied by functional changes in the epithelium including ion transport and impedance alterations. Early on in the process these take the form of increased impedance because of decreased specific electrogenic ion transport processes. As the tumor begins to develop in the pre-malignant epithelium, structural changes occur in the transformed cells such as a breakdown in tight junctions and nuclear atypia. The structural changes result in a marked reduction in the impedance of the tumor. The pattern and gradient of electrical changes in the epithelium permit the diagnosis of cancer from a combination of DC electrical and impedance measurements. Another reason that DC electropotential and impedance measurements have not been successfully applied to cancer diagnosis is that transepithelial potential and impedance may be quite variable and are affected by the hydration state, dietary salt intake, diurnal or cyclical variation in hormonal level, or non-specific inflammatory changes and other factors. In the absence of knowledge about the physiological variables which influence transepithelial potential and impedance these kinds of measurements may not be reliable to diagnose pre-malignancy or cancer. Furthermore a detailed understanding of the functional and morphological alterations that occur during carcinogenesis permits appropriate electrical probing for a specifically identified ion transport change that is altered during cancer development. For example knowledge that electrogenic sodium absorption is reduced during cancer development in the colon permits the use of sodium channel blockers (e.g., amiloride) or varying sodium concentration in the ECM to examine whether there is an inhibitable component of sodium conductance. By varying the depth of the measurement (by measuring the voltage drop across differently space electrodes), it is possible to obtain topographic and depth information about the cancerous changes in the epithelium.

The diagnostic accuracy of current technology using DC electropotentials or impedance alone has significant limitations. Sensitivity and specificity for DC electrical measurements in the breast have been reported as 90% and 55% respectively and 93% and 65% for impedance measurements. This would result in an overall diagnostic accuracy of between 72-79%, which is probably too low to result in widespread adoption. J. Cuzick et al. Electropotential measurements as a new diagnostic modality for breast cancer. *Lancet* 1998; 352 (9125): 359-363; A. Malich et al. Electrical impedance scanning for classifying suspicious breast lesions: first results. *Eur. Radiol.* 2000; 10(10): 1555-1561. The combination of DC electrical potentials and impedance spectroscopy may result in a diagnostic accuracy of greater than 90% which will lead to improved clinical utility.

Thus, there remains a need for effective, practical methods of detecting abnormal tissue.

SUMMARY OF THE INVENTION

To overcome problems and inadequacies associated with prior methods, abnormal or cancerous tissue is characterized using DC measurements and impedance measurements in combination. DC measurements provide information about the functional state of the epithelium and can detect early pre-malignant changes and an adjacent malignancy. Impedance measurements at different frequencies using differently spaced electrodes provide depth and topographic information to give both structural (high frequency range) and functional (low frequency range) information about the tissue being probed. Abnormal or cancerous tissue can be detected and characterized by detecting and measuring transport alterations in mucosal tissues, using ionic substitutions and/or pharmacological and hormonal manipulations to determine the presence of abnormal pre-cancerous or cancerous cells. A baseline level of transepithelial DC potential, impedance, or other electrophysiological property that is sensitive to alterations in transport in epithelia is measured in the tissue to be evaluated. An agent may be introduced to enhance the transport or make it possible to detect the transport alteration. The transepithelial DC potential and/or impedance of the tissue (or other electrophysiological property that may reflect or make it possible to detect alterations in the transport) are then measured. Based on the agent introduced and the measured electrophysiological parameter, the condition of the tissue is determined.

A method and system are provided for determining a condition of a selected region of epithelial tissue. At least two current-passing electrodes are located in proximity to or in contact with a first surface of the selected region of the tissue. Alternatively, the current passing electrodes may pass current across the tissue or epithelium. For example, current may be passed between the urethra and surface of the prostate, accessed per rectum; between the abdominal wall and the bowel mucosal surface; between the skin surface of the breast and the central breast ducts accessed by central duct catheter or ductoscope. A plurality of measuring electrodes are located in contact with or in proximity with the first surface of the selected region of tissue as well. A signal is established between the current-passing electrodes. One or more of the measuring electrodes measures impedance associated with the established signal. Alternatively a three electrode system may be used for measurements whereby one electrode is used for both current injection and voltage recording. An agent is introduced into the region of tissue. The condition of the tissue is determined based on the effect of the agent on measured DC transepithelial potential impedance or other electrophysiological characteristics. The electrodes in the described methods and apparatus can be used in contact with, in proximity to, over, or inserted into the tissue being examined. It should be understood that where the method is described in an embodiment as encompassing one of these arrangements, it is contemplated that it can also be used interchangeably with the other. For example, where the method is described as having an electrode in contact with the tissue, the method can also be used with the electrode inserted into or in proximity to the tissue. Similarly, where the method is described as having an electrode in proximity to the tissue, it is contemplated that the electrode can also be in contact with or inserted into the tissue. The method similarly contemplates measuring the real part (impedance known to be characterized mathematically by "real" and "imaginary" components) of a resulting potential difference measured over a current path across the current-passing electrodes.

In order to more accurately detect transport alterations in abnormal pre-cancerous or cancerous epithelial tissue, a pharmacological agent may be introduced to manipulate the tissue. Pharmacological agents may include agonists of specific ion transport and electrical activity, antagonists of specific ion transport and electrical activity, ionic substitutions, and/or hormonal or growth factor stimulation or inhibition of electrical activity.

Depending on the location of the tissue to be investigated, a number of methods may be used to administer the pharmacological or hormonal agents. One exemplary method includes introducing the agent directly to the tissue being investigated, via either direct contact or injection. Another exemplary method includes applying the agent to the skin surface, wherein the agent acts transcutaneously, or through the skin. Yet another exemplary method includes electroporation, wherein the epithelium or surface is made permeable by the passage of alternating current via electrodes in contact or penetrating the organ or epithelium of interest. The agent then passive diffuses into the organ and its constituent cells. Additional exemplary methods include via inhalation, oral administration, lavage, gavage, enema, parenteral injection into a vein or artery, sublingually or via the buccal mucosa, or via intraperitoneal administration. One skilled in the art will appreciate that other methods are possible and that the method chosen is determined by the tissue to be investigated.

Thus, systems and methods consistent with the present invention use a combination of transepithelial electropotential and impedance measurements to diagnose pre-malignancy or cancer. Further, systems and methods consistent with the present invention use a defined set of frequencies in combination to characterize functional and structural alterations in pre-malignancy and cancer. By using spaced electrodes the present invention may provide topographic and geometrical (depth) information about the epithelium under examination to diagnose pre-malignancy and cancer. In one embodiment, systems and methods of the present invention use electrodes with specially formulated ECMs to provide functional information about the epithelium to diagnose pre-malignacy and cancer.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate one embodiment of the invention and together with the description, serve to explain the principles of the invention. In the Figures.

DETAILED DESCRIPTION

Figure 1:
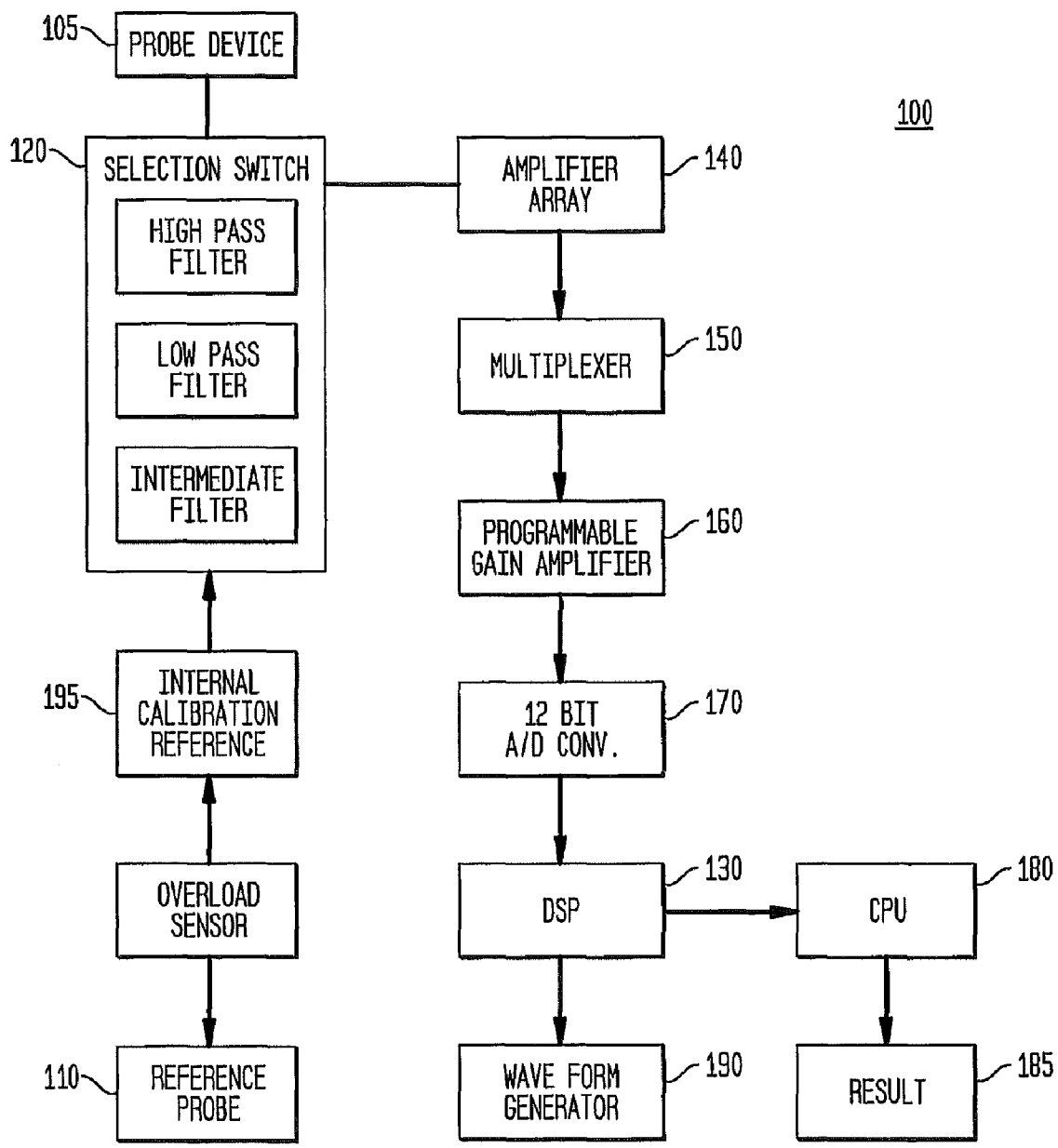
FIG. 1 is a schematic diagram of a DC and AC impedance measuring device, consistent with an embodiment of the present invention.

Reference will now be made in detail to an embodiment of the invention, an example of which is illustrated in the accompanying drawings. Wherever possible, the same reference numbers will be used throughout the drawings to refer to the same or like parts.

In order to combine DC transepithelial measurement with impedance measurements, it may be necessary to obtain baseline measurement of the DC potential using the voltage sensing electrodes, referenced to a low impedance surface electrode, or the blood stream via an IV, or the interstitial body fluid via a needle electrode or electrode that permeabilizes the overlying epidermis or other epithelium, or other body reference point. The electrodes may contain different ionic concentrations, pharmacological agents, or hormones in their ECMs. As used in this description, an ECM is a medium that permits transmission of electrical signals between the surface being measured and the electrode. An agent includes any ionic concentration, pharmacological agent, hormone, or other compound added to the ECM or otherwise introduced to the tissue under investigation, selected to provide further information about the condition of the tissue. In another embodiment the concentrations of agents may be changed using a flow through system.

In order to measure the depth of the impedance alteration, a voltage drop is made between electrodes with different spacing. Spacing is determined by knowledge of the depth to be probed. Similarly, two different frequency ranges will be used to measure functional and structural changes at different depths.

In order to more accurately detect the functional transport alterations at different depths in abnormal pre-cancerous or cancerous epithelial tissue, an agent, such as a pharmacological agent, may introduced to manipulate the tissue, while electrically probing the tissue at different frequencies and monitoring the voltage drop between differently spaced electrodes. Pharmacological agents include agonists of specific ion transport and electrical activity, antagonists of specific ion transport and electrical activity, ionic substitutions, and/or hormonal or growth factor stimulation, which modulates, inhibits or stimulates electrical activity.

Depending on the location of the tissue to be investigated, a number of methods may be used to administer the pharmacological or hormonal agents. One exemplary method includes introducing the agent directly to the tissue being investigated, via either direct contact or injection. Another exemplary method includes applying the agent to the skin surface, wherein the agent acts transcutaneously, or through the skin. Another exemplary method includes electroporation, wherein the epithelium or surface is made permeable by the passage of alternating current via electrodes in contact with or penetrating the organ or epithelium of interest. The agent then passively diffuses into the organ and its constituent cells. Additional exemplary methods include via inhalation, oral administration, lavage, gavage, enema, parenteral injection into a vein or artery, sublingually or via the buccal mucosa, or via intraperitoneal administration. One skilled in the art will appreciate that other methods are possible and that the method chosen is determined by the tissue to be investigated.

Based on the agent introduced and the tissue being investigated, measurements of electrophysiological properties, such as impedance, are performed. Other properties that can be measured includes, transepithelial potential, changes in spontaneous oscillations in transepithelial potential or impedance associated with the malignant state, and time delay in a propagation signal between electrodes, which indicates a change or loss of gap-junction function. The results of these measurements are then used to determine the condition of the investigated tissue. For example, research has indicated that specific ion transport processes are altered during the development of cancer. For example, a loss of electrogenic $Na^+$ transport, an up-regulation in Na/H exchange, a down-regulation in $K^+$ conductance, a decrease in basal $Cl^-$ absorption, and a down-regulation in c-AMP (cyclic adenosine-3', 5'-cyclic monophosphate) stimulated $Cl^-$ secretion have been observed.

Thus, by administering agents appropriate to the particular epithelial tissue and measuring the associated electrophysiological characteristics, it is possible to detect abnormal pre-cancerous or cancerous tissue while the development of such tissue is at an early stage. The method and system of the present invention is applicable to any epithelial derived cancer, such as, but not limited to, prostate, colon, breast, esophageal, and nasopharyngeal cancers, as well as other epithelial malignancies, such as lung, gastric, uterine cervix, endometrial, skin, and bladder.

Specifically, in cancers affecting mucosal or epithelial tissues, transport alterations may be sufficiently large to suggest that they are a consequence of an early mutation, affecting a large number of cells (i.e., a field defect). In this case, they may be exploited as potential biomarkers for determining which patients should be either more frequently monitored, or conversely, may be used to identify particular regions of mucosa that require biopsy. The latter is especially helpful in the case of flat adenomas or dysplasia, which are more difficult to detect physically than, for example, polyps.

A number of variations are possible for devices to be used with the present invention. Further, within a device design, there are a number of aspects that may be varied. These variations, and others, are described below.

One probe or other device includes a plurality of miniaturized electrodes in recessed wells. Disposable commercially available silicon chips processing, such as filtering, may perform surface recording and initial electronic processing. Each ECM solution or agent may be specific to the individual electrode and reservoir on the chip. Thus, for one measurement, a particular set of electrodes is used. For another measurement, for example, at a different ionic concentration, a different set of electrodes is used. While this produces some variations, as the electrodes for one measurement are not located at the same points as for another, this system provides generally reliable results.

An alternative approach is to use fewer electrodes and use a flow-through or microfluidic system to change solutions and agents. Specifically, solutions or agents are changed by passing small amounts of electrical current to move solution or agent through channels and out through pores in the surface of the probe. In this embodiment, the electrode remains in contact with the same region of the epithelium, thus eliminating region-to-region variation in measurement. This approach requires time for equilibration between different solutions.

In detecting the presence of abnormal pre-cancerous or cancerous breast tissue, a hand-held probe is provided for obtaining surface measurements at the skin. The probe may include electrodes for passing current as well as for measuring. An impedance measurement may be taken between the nipple cup electrode and the hand-held probe, or may be taken between electrodes on the hand-held probe. After taking initial DC measurements, a wetting/permeabilizing agent may be introduced to reduce skin impedance. The agent may be introduced using a microfluidic approach, as described above, to move fluid to the surface of the electrodes. Alternatively, surface electrodes that just penetrate the stratum corneum may be used to decrease impedance.

Regardless of the configuration of the device, FIG. 1 is a schematic of a DC and AC impedance measurement system 100 used in cancer diagnosis, consistent with the present invention. The system 100 interfaces with a probe device 105 including multiple electrodes, wherein the actual implementation of the probe device 105 depends on the organ and condition under test. The probe device 105 may incorporate the electrodes attached to a glove, needle, body cavity, endoscopic, or surface probe. A reference probe 110 may take the form of an intravenous probe, skin surface probe, or epithelial surface reference probe depending on the test situation and organ under investigation.

To avoid stray capacitances, the electrodes may be connected via shielded wires to a selection switch 120 which may select a specific probe 105 following a command from the Digital Signal Processor (DSP) 130. The selection switch 120 also selects the appropriate filter interfaced to the probe 105, such that a low pass filter is used during DC measurements and/or an intermediate or high pass filter is used during the AC impedance measurements. The selection switch 120 passes the current to an amplifier array 140 which may be comprised of multiple amplifiers or switch the signals from different electrodes through the same amplifiers when multiple electrodes are employed. In a preferred embodiment digital or analogue lock-in amplifiers are used to detect minute signals buried in noise. This enables the measurement of the signal of interest as an amplitude modulation on a reference frequency. The switching element may average, sample, or select the signal of interest depending on the context of the measurement. This processing of the signal will be controlled by the DSP following commands from the CPU. The signals then pass to a multiplexer 150, and are serialized before conversion from an analogue to a digital signal by the ADC. A programmable gain amplifier 160 matches the input signal to the range of the ADC 170. The output of the ADC 170 passes to the DSP 130. The DSP 130 processes the information to calculate the DC potential and its pattern on the epithelial or skin surface as well as over the region of suspicion. In addition the impedance at varying depth and response of the DC potential and impedance to different ECM concentrations of ions, drug, hormones, or other agent are used to estimate the probability of cancer. The results are then sent to the CPU 180 to give a test result 185.

Alternatively the signal interpretation may partly or completely take place in the CPU 180. An arbitrary waveform generator 190 or sine wave frequency generator will be used to send a composite waveform signal to the probe electrodes and tissue under test. The measured signal response (in the case of the composite wave form stimulus) may be deconvolved using FFT (Fast Fourier Transforms) in the DSP 130 or CPU 180 from which the impedance profile is measured under the different test conditions. An internal calibration reference 195 is used for internal calibration of the system for impedance measurements. DC calibration may be performed externally, calibrating the probe being utilized against an external reference electrolyte solution.

Figure 2:
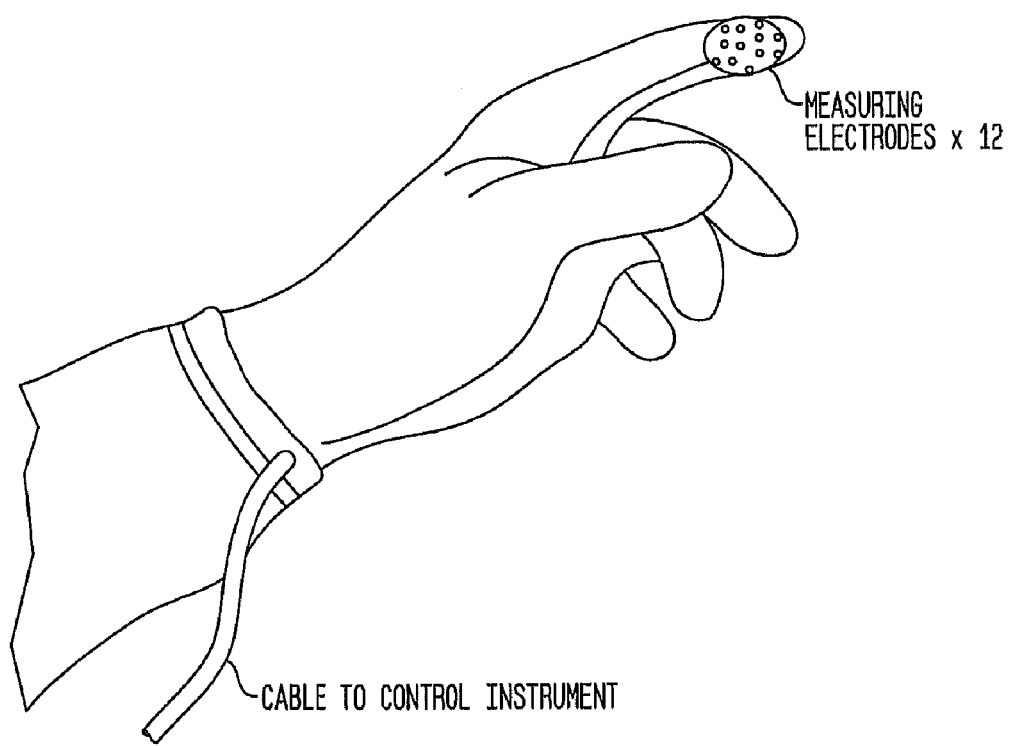
FIG. 2 illustrates an exemplary embodiment of a device suitable for use with systems and methods consistent with the present invention.

FIG. 2 illustrates a glove that may be used, for example, in diagnosis of prostate cancer or as a screening test for colorectal neoplasia. Multiple sensor electrode arrays may be attached to an examining glove together with current passing electrodes. The individual electrodes may be recessed and ECMs with different composition may be used to pharmacologically, electrophysiologically, or hormonally probe the epithelium under test. Spacing of the electrodes may be greater for the prostate configuration than for other organ systems so that deeper tissue may be electrically probed and the impedance of the deeper tissue evaluated. The electrodes will be interfaced via electrical wire, or wireless technology, with the device described in FIG. 1 above.

Figure 3:
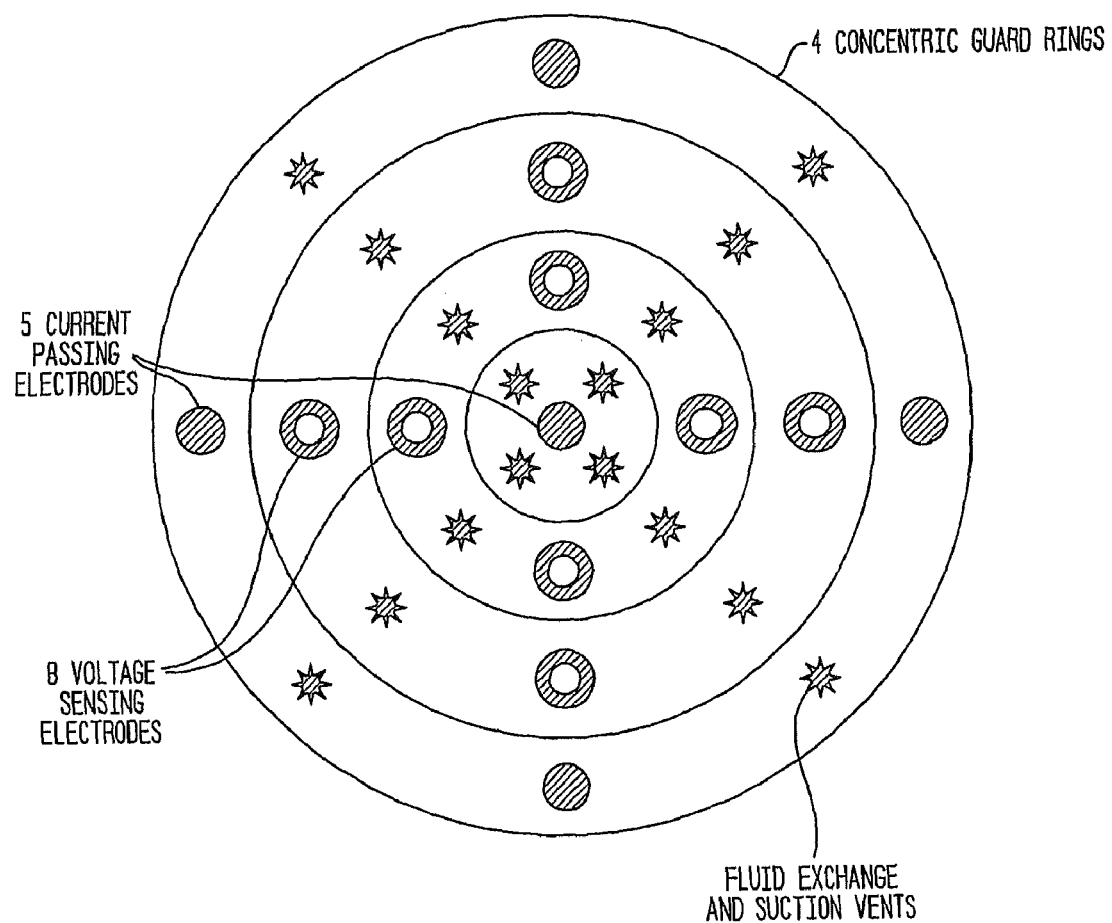
FIG. 3 illustrates another exemplary embodiment of a device suitable for use with systems and methods consistent with the present invention.

FIG. 3 is a schematic of an endoscopic probe, consistent with the present invention, which may be placed in contact with the epithelium endoscopically. This probe may either be placed passively in contact with the epithelium or held in place by pneumatic suction over the region of interest. Ports are in place for the exchange of solutions or for fluid exchange and suction. Guard rings may be incorporated to prevent cross-talk between electrodes and to force current from the contact surface into the epithelium. In this configuration there are four current passing electrodes each positioned radially 90° apart. This permits current to be passed and the voltage response to be measured in perpendicular fields. This enables the effects of surface asymmetry on impedance (such as occurs with aberrant crypt foci) to be measured. Electrodes may be slightly recessed so as not to influence current density measured at the surface.

Figure 4A:
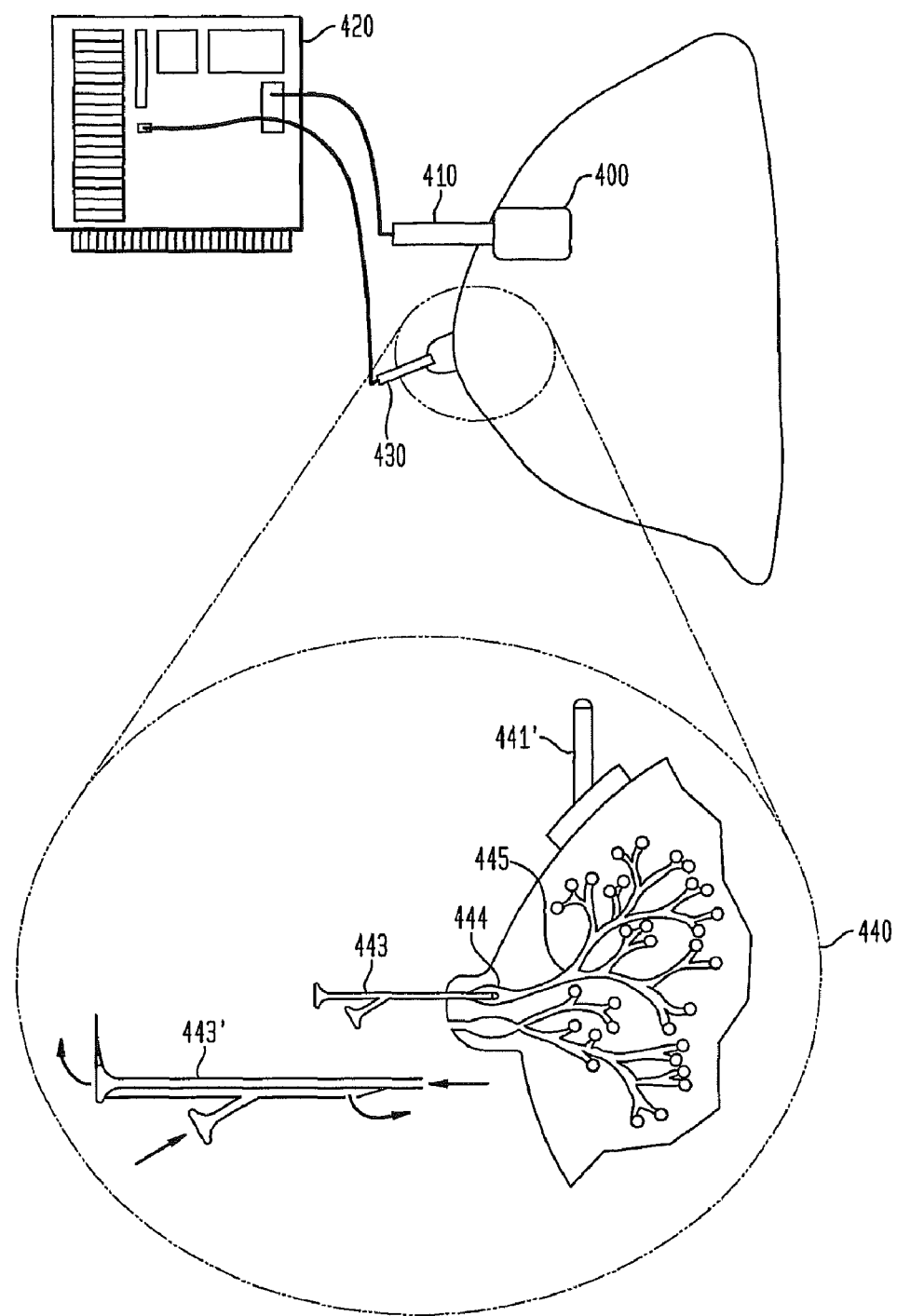
FIGS. 4A and 4B illustrates other exemplary embodiments of a device suitable for use with systems and methods consistent with the present invention.

FIG. 4A includes a handheld probe 400, consistent with the present invention, which may be applied to the surface of the breast. The probe may include a handle 410. The probe 400 may be attached, either directly or indirectly using, for example, wireless technology, to a measurement device 420. The probe 400 may be referenced to an intravenous electrode, a skin surface electrode, or other ground. In one embodiment, illustrated in FIG. 4A, the reference is a nipple electrode or ductal probe 430, illustrated in greater detail at close-up 440. One advantage of this configuration is that DC electropotential and impedance can be measured between the nipple electrode 430 and the probe 400. The measurement is thus a combination of the DC potentials and impedance of the breast ductal epithelium, non-ductal breast parenchyma, and the skin.

Referring to close-up 440, the ductal probe is inserted into one of several ductal orifices that open onto the surface of the nipple. Ductal probe 443 is shown within a ductal sinus 444, which drains a larger collecting duct 445.

Another advantage of using a nipple electrode is that a solution for irrigating the ductal system may be exchanged through the probe, permitting introduction of pharmacological and/or hormonal agents. As shown in magnified nipple probe 443, 443' fluid can be exchanged through a side port. Fluid may be infused into the duct and aspirated at the proximal end (away from the nipple) of the nipple probe. Different electrolyte solutions may be infused into the duct to measure altered permeability of the ductal epithelium to specific ions or the epithelium may be probed with different drugs to identify regions of abnormality. Estradiol, or other hormonal agents, may be infused into a breast duct to measure the abnormal electrical response associated with pre-malignant or malignant changes in the epithelium.

It should be understood that different configurations may also be used, such as a modified Sartorius cup that applies suction to the nipple. With this configuration, gentle suction is applied to a cup placed over the nipple. Small amounts of fluid within the large ducts and duct sinuses make contact with the electrolyte solution within the Sartorius cup, establishing electrical contact with the fluid filling the breast ducts. DC or AC measurements may then be made between the cup and a surface breast probe.

Figure 4B:
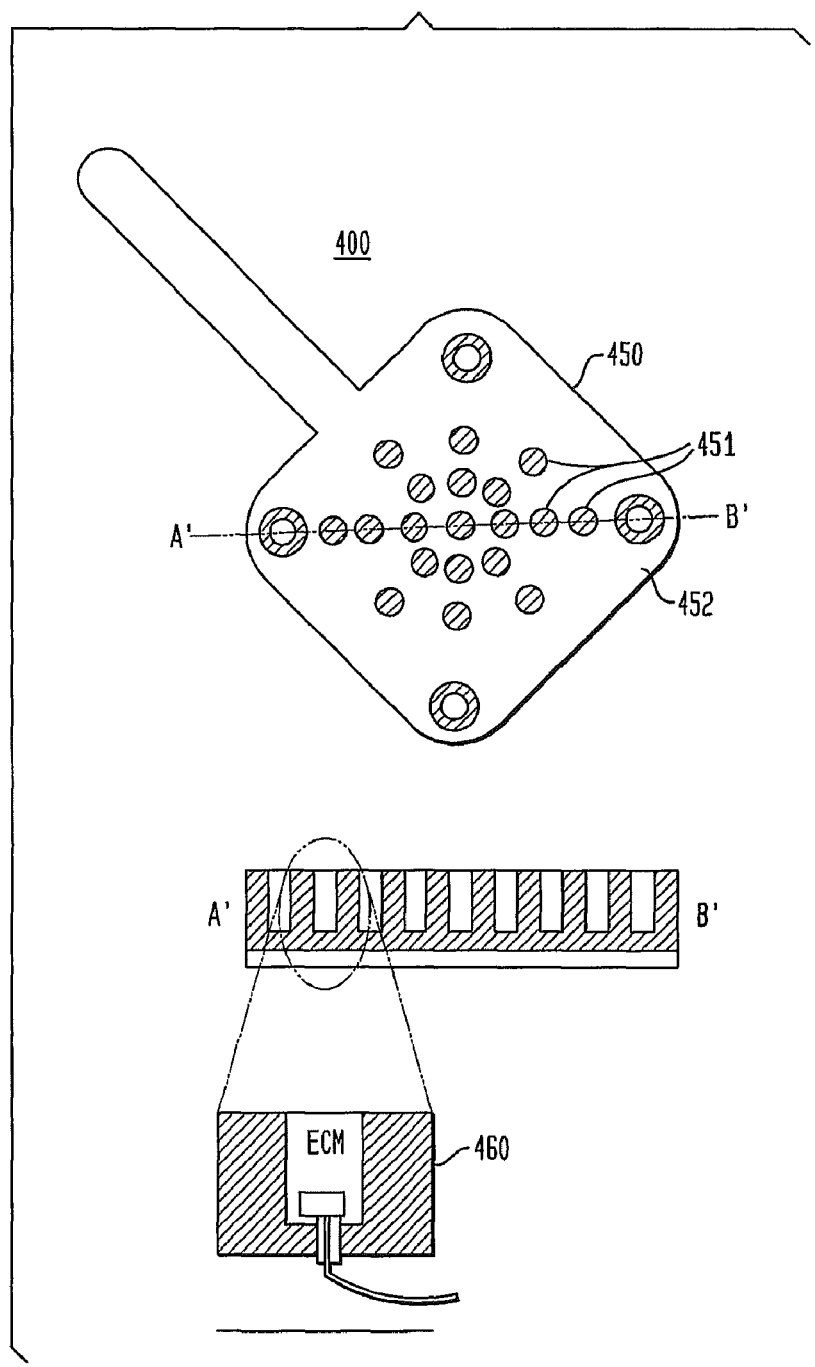

FIG. 4B illustrates the probe 400 of FIG. 4A in greater detail. The skin contact of the surface 450 is placed in contact with the breast. The surface electrodes 451 measure DC or AC voltages. The current passing electrodes 452 are used for impedance measurements. Probe 400 may also include one or more recessed wells containing one or more ECMs.

Further embodiments of this technique may involve the use of spaced electrodes to probe different depths of the breast, and the use of hormones, drugs, and other agents to differentially alter the impedance and transepithelial potential from benign and malignant breast tissue, measured at the skin surface. This enables further improvements in diagnostic accuracy.

EXAMPLE 1

Colon Cancer

In colon cancer, the following electrophysiological changes have been observed during the development of the abnormal tissue: loss of electrogenic $Na^+$ transport, up-regulation in Na/H exchange, down-regulation in $K^+$ conductance, decrease in basal $Cl^-$ absorption, and down-regulation in c-AMP (cyclic adenosine-3',5'-cyclic monophosphate)

stimulated Cl⁻ secretion. A number of pharmacological and hormonal manipulations can be performed to detect these ion transport alterations.

By using electrolyte conductive medium (ECM) of different concentrations, the conductance of specific ions can be estimated and the response to different pharmacological probes can be determined. Different pharmacological agents are administered that influence electrophysiological properties of normal bowel, but have minimal or different effects on pre-cancerous or cancerous tissue. For example, glucocorticoids or mineralocorticoids, administered by injection or orally, increase the transepithelial electropotential (TEP) of normal colon, but have a lesser effect on pre-cancerous or cancerous tissue. These steroids up-regulate electrogenic sodium absorption, thereby decreasing sodium specific impedance in normal colon.

The measured TEP decreases in response to a topically applied amiloride (a sodium channel blocker) in normal colonic mucosa. This response is reduced by approximately 50% in pre-cancerous mucosa or by greater than 75% in cancerous mucosa. In addition, the loss in sodium conductance results in an increase of impedance of the surface epithelium. This ion transport alteration may be measured by determining the change in TEP as well as the basal impedance. In abnormal pre-cancerous or cancerous tissue, the TEP is lower, the response of the TEP to amiloride is less, and the increase in impedance (observed in normal colon in response to amiloride) is less in abnormal pre-cancerous or cancerous tissue. Similar pharmacological agents may be introduced that alter the effect of chloride or potassium ion transport, which affect abnormal pre-cancerous or cancerous tissue in a different manner than in normal colon tissue.

It is important to note that the impedance is higher, or conductance is generally lower, around the edge of the tumor or in the immediately adjacent pre-malignant epithelium. At more than 5-10 cm from the tumor the TEP is lower and ion specific impedances may be higher. In the tumor itself the impedance is lower (conductance higher). Measurement may be made over a suspected tumor, but also adjacent and some distance away from the suspected tumor to more accurately identify the cancerous or pre-cancerous tissue. There are also pharmacological differences between normal pre-cancerous and cancer tissue. Direct comparison between these different regions can used to make a more accurate diagnosis of cancer or premalignancy.

In one embodiment, electrophysiological measurements are performed using a series of two or more electrodes attached to an examining glove or probe. Some factors influencing the spacing of the electrode and the signal used include the depth of penetration desired and permeabilization of the surface epithelium using penetrating agents. A probe that permits variable frequency signals and varying electrode placement provides the most versatile arrangement, but a probe or glove providing a single frequency signal and/or static electrode placement may also be used.

Sodium: Sodium conductance and absorptive properties in the surface cells of the colonic epithelium are markedly attenuated in some pre-cancerous and cancerous cells. By measuring the impedance of the colonic epithelium using low frequency sine waves and closely placed electrodes, it is possible to determine the electrophysiological activity of the surface cells. Passive electrodes, placed between current-passing electrodes, measure the impedance, while ECMs of different sodium concentration may be used to reveal alterations of the specific ionic permeabilities of the epithelium. By using higher frequency sine waves and widely spaced electrodes and ECMs of varying sodium concentration, it is possible to estimate overall and ion-specific conductances of the deeper epithelium. A ratio may be determined, expressed as the change in surface to deep sodium conductance. The surface/deep sodium conductance ratio progressively decreases as tissue develops from at-risk, to pre-cancerous to cancerous tissue. The surface cells that are conductive to sodium are replaced by cells from the deeper epithelium that do not have as high a conductance. Therefore, the ratio of surface $Na^+$ conductance/deep $Na^+$ conductance goes from >2.0 to <1.0. Both the ratio and absolute number change. Measuring the ratio effectively normalizes the measurement for the particular individual and epithelial region under test.

A number of ECMs and pharmacological agents may be employed to characterize the sodium transport characteristics of colonic tissue. In one exemplary method, initial measurements are made using an electrolyte solution containing 10 mM KCl in the ECM, either in gel or solution, which interfaces between the electrode and the bowel wall. Measurements are taken relative to an intravenous reference electrode or a low impedance skin electrode, having a minimal offset voltage relative to the underlying extracellular fluid and bloodstream. The TEP is then measured at increasing levels of sodium, both in the absence and presence of amiloride or similar agent, such as benzamil, (10 μM-1 mM) to block electrogenic sodium transport. The difference between the two measurements will be the TEP attributable to the electrogenic sodium transport across the bowel epithelium. The electrogenic component of sodium transport is diminished by 40-50% in colonic epithelium that is at-risk or pre-cancerous.

One method for varying the sodium and/or pharmacological content during measurement include using one or more wells or reservoirs associated with each electrode, containing different concentrations of electrolyte and/or agent, so that the solution is not actually changed during measurement but the measurement occurs under different conditions with different electrodes and ECMs. Another method involves a flow-through solution change system, whereby solution changes may be automated while using fewer electrodes.

Potassium: Measurements similar to that described above, with reference to sodium, are performed with reference to potassium. Specifically, an early decrease in potassium conductance is associated with at-risk or pre-cancerous colonic epithelium. As cancer develops, potassium conductance becomes up regulated and potassium secretion may be enhanced. The decrease, and then increase, in potassium conductance enables not only identification of abnormal tissue, but also the determination of the condition of the tissue, as either normal, at-risk, pre-cancerous, or cancerous.

Impedance measurements may be performed at varying concentrations of potassium, using signals of varying frequency, and using variably spaced electrodes, thus providing an impedance profile including the superficial and deep epithelium. For example, one method of determining an impedance profile, with reference to potassium, is as follows: A TEP measurement is made using increasing concentrations of $K^+$ and all measurements are performed using ECM containing amiloride or another blocker of the electrogenic $Na^+$ pump to remove the contribution of electrogenic $Na^+$ transport to TEP. Using the well method described above, the ECM in each well contains a combination of amiloride, bethanacol, forskolin, and 3-isobutyl-1-methylxanthine (IBMX). Each of the four wells contains varying $K^+$ concentrations (between 10 and 80 mM), while maintaining the concentration of Na and Cl ions. These agents (bethanacol, forskolin, and IBMX) depolarize the cell membrane by maximally opening $Cl^-$ conduction channels in the surface cells of the colon. This cell membrane depolarization results in the opening of voltage-sensitive $K^+$ channels in the cell membrane. Specifically, bethanacol (or carbacol) raises intracellular $Ca^{2+}$ which opens $Ca^{2+}$ sensitive $K^+$ channels, as well as increasing chloride secretion opening up $Cl^-$ channels. Other muscarinic agonists may produce similar results. Forkskolin increases adenyl cyclase, thereby raising intracellular c-AMP opening up $K^+$-channels. IBMX, a phosphodiesterase inhibitor, may be used to raise c-AMP. Other agents, such as theophylline, may also be used to raise c-AMP. Agents, such as dibutyrl c-AMP, may be used to increase c-AMP directly. These agents maximally increase potassium conductance and secretion, permitting the identification of reduced potassium secretion and conductance associated with at-risk or pre-cancerous tissue.

Another such method employs measurements with a series of varying KCl concentrations in contact with the colonic mucosa, such as 10, 20, 40, and 80 mM KCl. Electrodes containing 10 μM-1 mM amiloride in the ECM are used to measure TEP and impedance, both in the presence and absence of $K^+$-channel blockers, such as 20 mM. TEA (tetraethyl ammonium) and 5 mM barium. The TEP is lower than normal in the at-risk and pre-cancerous tissue. The impedance is lower than normal in the cancerous tissue. In transitional tissue or tissue adjacent to developing cancer, impedance may be higher than normal.

Chloride: Similar to the methods for sodium and potassium described above, chloride conductance can be used to determine abnormal pre-cancerous and cancerous tissue. Chloride conductance occurs mainly at the base of the crypt (or deep) in normal epithelium. In cancerous tissue, the epithelial cells closer to the surface of the crypt become more conductive to chloride, albeit at a lower level of conductance than observed in the base. The ratio of chloride conductance between the surface and the base, as estimated from impedance measurements, can be used to characterize colonic tissue as either normal, at-risk, pre-cancerous, or cancerous. Specifically, at-risk and pre-cancerous epithelium exhibits an overall decrease in chloride conductance, with an increase in the surface/base ratio. As the tissue progresses to cancerous, the overall chloride conductance increases and is accompanied by increased $Cl^-$ secretion. The surface/base ratio may become less discriminatory, however, because normal epithelial morphology is lost in a malignant tumor.

As with potassium, chloride-dependent TEP is measured using increasing concentrations of $Cl^-$. Measurements are made in the presence of an ECM containing a sodium pump blocker agent, such as amiloride, in order to negate the contribution of electrogenic $Na^+$ transport, and agents, such as bethanacol, forskolin, and IBMX to maximally open $Cl^-$ conduction channels in the surface cells of the colon. The wells have $Cl^-$ concentrations varying between 15 and 120 mM, while maintaining the concentrations of Na and K ions and keeping osmolality constant. In at-risk and pre-cancerous tissue, the $Cl^-$ is reduced. Additionally, the TEP is lower than normal. In cancerous tissue, the basal $Cl^-$ secretion and $Cl^-$ conductance is increased.

Drug Provocation: In addition to the ionic manipulations described above, the colon responds to a number of different hormones, growth factors, and diets by changing the ion transport characteristics of the epithelium. For example, aldosterone (a mineralocorticoid) and dexamethasone (a glucocorticoid) both increase electrogenic sodium absorption and potassium secretion in the colon. In normal colon, sodium conductance is increased in surface cells and the epithelium hyperpolarizes, or becomes more negative in the lumen. Potassium conductance increases in the deeper cells. In at-risk, pre-cancerous, or cancerous tissue, however, this response is significantly different. The hyperpolarization and increase in sodium conductance is markedly diminished. The increase in the potassium conductance in the basal cells of the crypt is much less than occurs in normal colon. Thus, agents and treatments that affect the ion transport characteristics of the epithelium may be used to enhance differences between normal and abnormal colon tissue in impedance measurements and/or other measurements of the electrical characteristics. A high-potassium, low-sodium diet will produce similar effects in a normal bowel. Other agents may be administered directly to the surface of the bowel and produce similar effects in normal epithelium. Carbenoxolone, for example, when administered rectally, increases TEP in normal bowel, but has a lesser effect on pre-cancerous or cancerous tissue. It causes an increase in TEP because it inactivates 11β-HSD (11-beta hydroxysteroid dehydrogenase). Cortisol has mineralocorticoid effects on the bowel and increases electrogenic sodium absorption and therefore increases TEP in normal but not in abnormal or cancerous bowel epithelium.

Figure 5A:
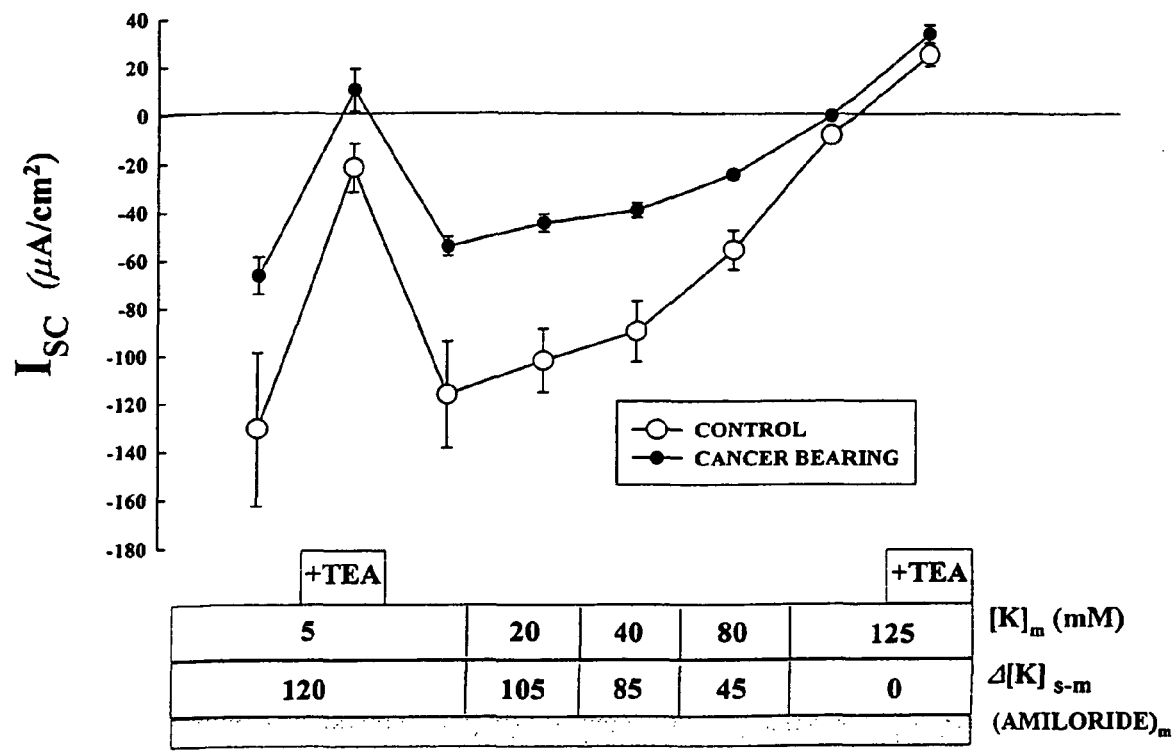
FIGS. 5A and 5B illustrate the short circuit current associated with human colonic epithelium ex-vivo.

FIG. 5A demonstrates the short circuit current of human colonic epithelium ex-vivo. The figure demonstrates the time course along the x-axis while varying the potassium gradient across the tissue. The potassium permeability of the apical membrane of human colonic mucosa ($P^K_a$) was determined in surgical specimens of controls and grossly normal-appearing mucosa obtained 10-30 cm proximal to colorectal adenocarcinomas. The mucosa was mounted in Ussing chambers and the basolateral membrane resistance and voltage were nullified by elevating the $K^+$ in the serosal bathing solution. The apical sodium ($Na^+$) conductance was blocked with 0.1 mM amiloride. This protocol reduces the equivalent circuit model of the epithelium to an apical membrane conductance and electromotive force in parallel with the paracellular pathway as has been verified by microelectrode studies. Increasing serosal $K^+$ caused the $I_{sc}$ to become negative (−140 μA/cm²) in normal colon after which 30 mM mucosal TEA caused an abrupt increase in $I_{sc}$ corresponding to block of apical $K^+$ channels. In cancer-bearing colon the reduction in $I_{sc}$ is to −65 μA/cm². The serosal bath was remained constant at 125 mM [K].

Figure 5B:
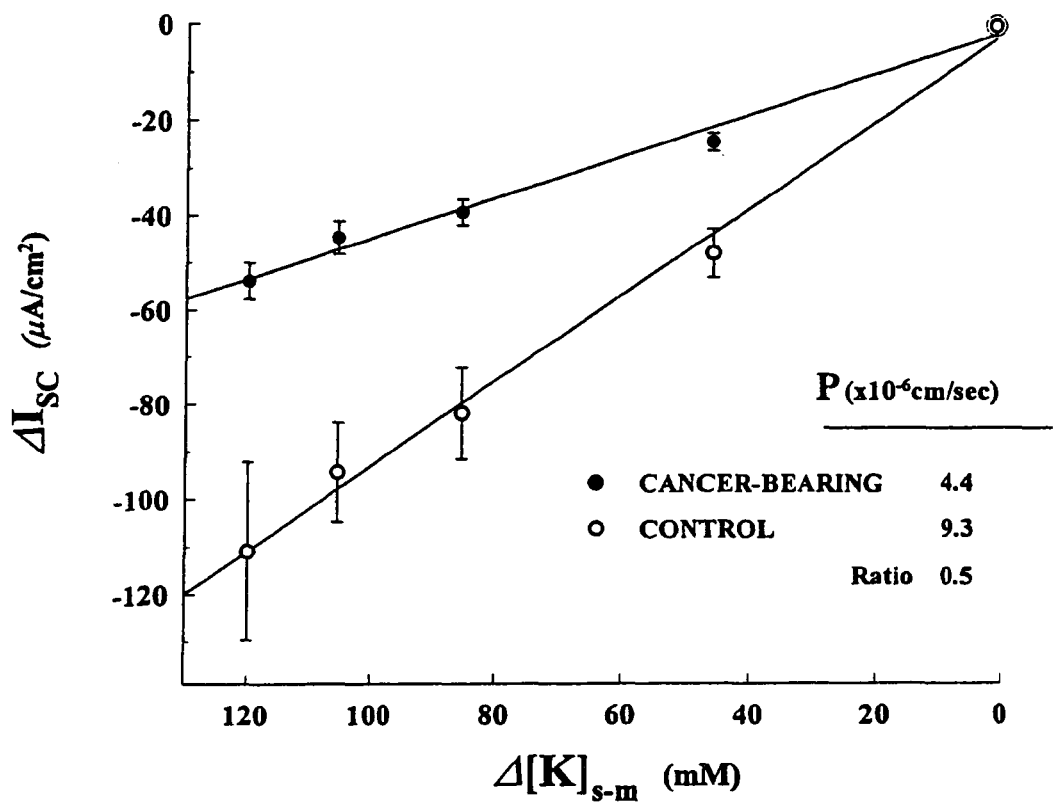

FIG. 5B demonstrates that $\Delta I_{sc}$, determined with respect to the $I_{sc}$ at 125 mM mucosal K, is a linear function of the concentration gradient, $\Delta[K]$. Because the voltage across the apical membrane is zero under these conditions and the paracellular pathway is nonselective, the $p^K_a$ (apical potassium permeability) can be calculated using the Fick equation—i.e., $I_{sc}=F \times P^K_a \Delta[K]$ where F is the Faraday constant and $\Delta[K]$ is the concentration difference for $K^+$ across the epithelium. FIG. 5b demonstrates mean±sem values for $I_{sc}$ in both normal and premalignant human distal colon. The apical $K^+$ permeability of controls was $9.34 \times 10^{-6}$ cm/sec and this was significantly reduced by 50% in premalignant human mucosa to $4.45 \times 10^{-6}$ cm/sec. $P^K_a$ could also be calculated for the change in $I_{sc}$ when the $K^+$ channels were blocked with TEA, assuming complete block. This resulted somewhat lower values of $6.4 \times 10^{-6}$ cm/sec and $3.8 \times 10^{-6}$ cm/sec corresponding to a 40% reduction in $P^K_a$.

These observations show that there is a field change in the $K^+$ permeability and conductance of human colon, during the development of cancer. Impedance measurements, DC measurement using electrodes with different potassium gradients together with specific drugs, such as amiloride to block the contributions of electrogenic $Na^+$ transport to the electrical properties of the bowel are useful to diagnose colon cancer.

Figure 6:
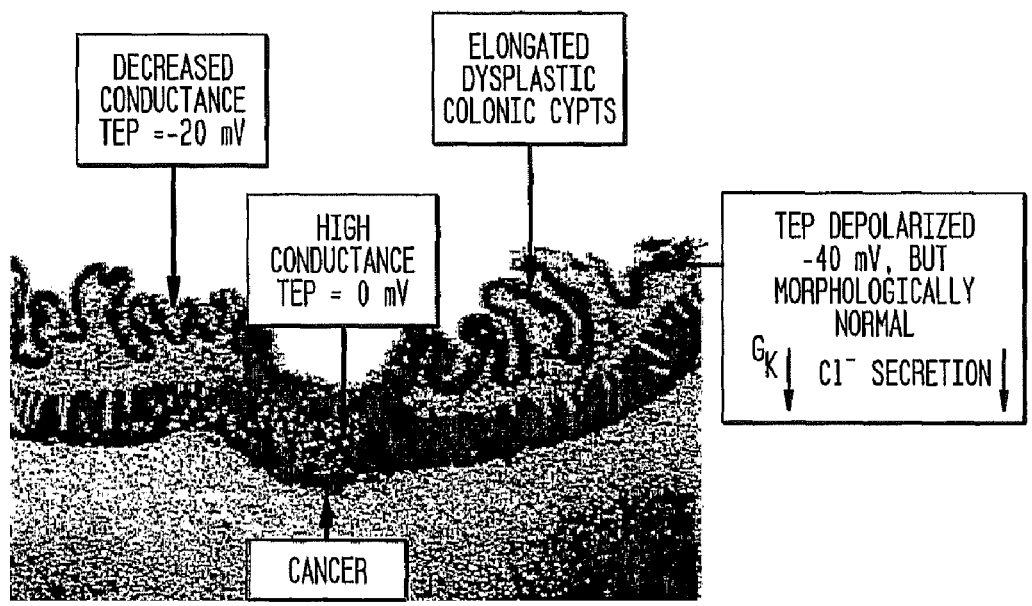
FIG. 6 is a photomicrograph illustrating electrophysiologic and histologic alterations that may be present in colonic cancer.

FIG. 6 is a photomicrograph which illustrates some of the complexities associated with electrophysiological and histological alterations that occur in the development of colonic cancer. The cancer is a 10 mm in diameter, invasive and an ulcerated lesion that could easily be missed at colonoscopy (because it is a depressed lesion). The cancer is depolarized to 0 mV with a much higher conductance than the surrounding epithelium. The surrounding or adjacent epithelium is also depolarized at about −20 mV but has a higher impedance than the cancer or normal epithelium. Note that the darker layer, the epithelium (e), is on the top surface. This is one cell layer thick, but form crypts, like inverted test tubes with proliferation and secretory function at the base and differentiated cells and absorptive function at the mouth. The inferior layer (m) is the muscle layer of the bowel. This small tumor has already invaded the muscle layer. More distant epithelium is also depolarized but to a lesser degree at −40 mV. Potassium conductance is decreased in this morphologically normal-appearing epithelium. Chloride secretion is also decreased compared to the tumor, which may actively secrete chloride. The sodium conductance, $G_{Na}$, is decreased and the Na/H exchanger is upregulated. The colonic mucosa tends to be thickened with elongated crypts in the region of the developing cancer (adjacent zone). Most of the impedance resides in the epithelial layer, and therefore a higher impedance below 750 μm indicates an epithelial thickening associated with cancer. Recognizing the electrophysiological pattern enables a diagnosis of cancer to be made, i.e. an electrophysiological virtual biopsy.

Figure 7:
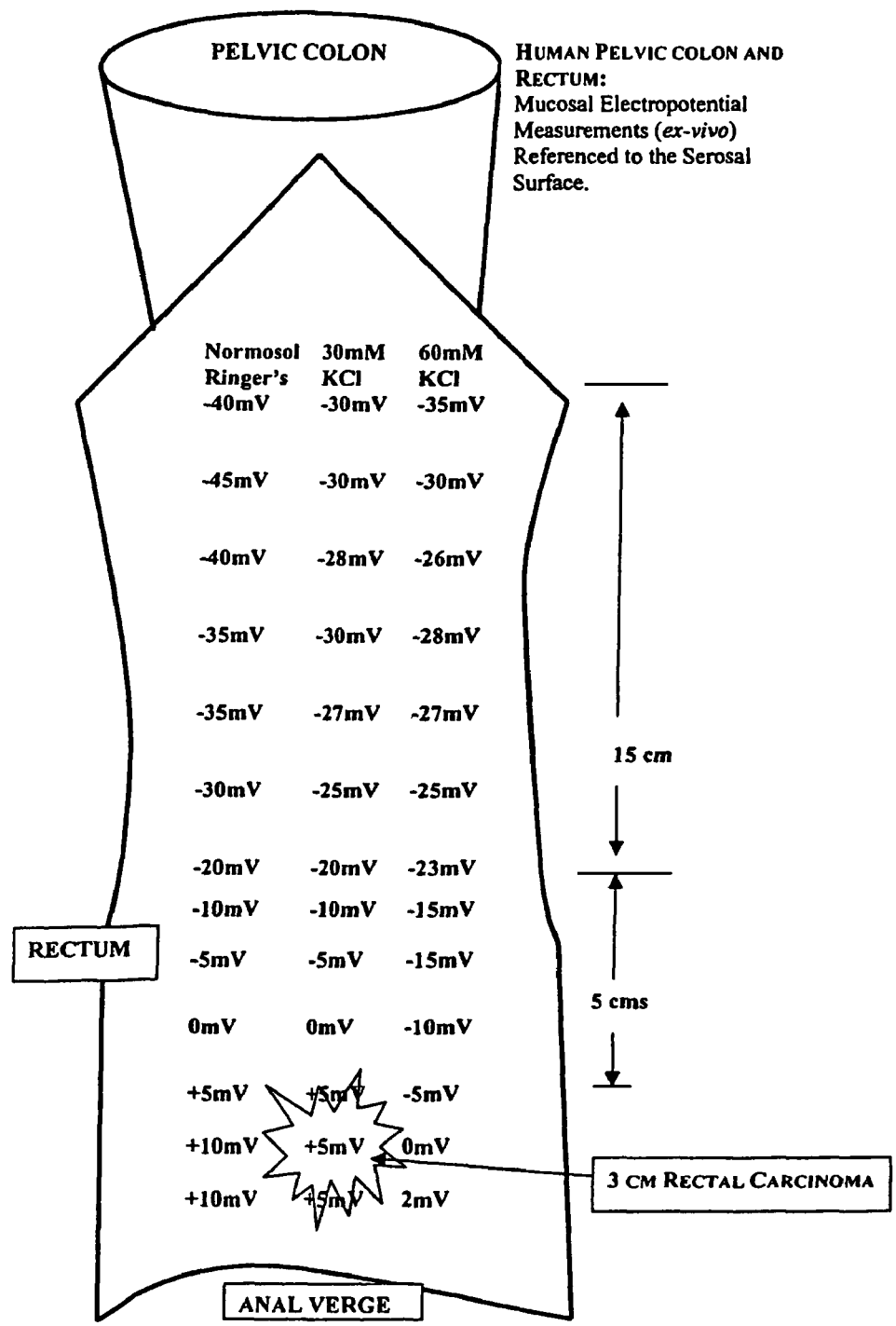
FIG. 7 illustrates measurements of epithelial electropotential in a patient with rectal cancer.

FIG. 7 demonstrates measurements of surface mucosal (epithelial) electropotential referenced to the serosal surface on a freshly excised specimen of pelvic colon and rectum from a 45-year-old male with an ulcerated rectal carcinoma. Following resection the specimen was immediately opened in a longitudinal direction and surface electropotential measurements were made using different ECMs. Following excision there is usually a decrease in the electropotential ("rundown") of 5-10 mV in the first 5-10 minutes, although the relative electropotential differences from region to region remain similar.

The "starburst" at the lower end of the figure, 2-3 cms from the anal canal and 5 cms from the anal verge has an electropotential of +10 mV measured over the surface of the tumor (left hand column "Normosol Ringers's"). Normosol Ringer's is a physiological saline solution containing approximately 5 mM $K^+$. The normal mucosal surface electropotential is −50 to −70 mV in the rectum. As measurement are taken some distance from the tumor the bowel remains depolarized even up to 20 cm from the edge of the tumor where readings of −40 to −45 mV are observed. This region is depolarized relative to normal colon where levels of less than −50 mV are observed.

When electropotential measurements are made in normal colon using an ECM with a higher $K^+$ concentration an increase in electropotential (increased positivity) of 20 mV or greater is frequently observed. This is because the normal colon is selectively permeable to K+ and the increased ECM $K^+$ concentration sets up a diffusion potential for $K^+$ across the ion-selective conductance pathways. In the cancer bearing colon $K^+$ conductance decreases in the region of the developing tumor as well as some distance from it ("field-cancerization"). Up to 5 cm from the developing cancer there is essentially no change in the measured electropotential when the ECM is changed from 5 to 30 mM $K^+$ (change from left column ("Normosol Ringer's") to middle column "30 mM KCl" in figure). Up to 20 cm from the tumor the change in electropotential does not exceed 15 mV (−45 to −30 mv) 20 cms from the edge of the tumor. A further increase in the $K^+$ concentration of the ECM results in small increases in positivity away from the tumor or an anomalous decrease in positivity near or at the tumor, suggesting that a diffusion gradient for a different ion (other than $K^+$) is set-up in the vicinity of the tumor.

Depolarization in combination with altered $K^+$ conductance and permeability may be used to diagnose the presence of cancer or increased risk of cancer. Altered $K^+$ conductance is observed before tumors develop in the bowel. Combination with simultaneous impedance measurements increases diagnostic accuracy.

EXAMPLE 2

Breast Cancer

As mentioned above, impedance and DC electrical potential have been used separately at the skin's surface to diagnose breast cancer. In the current invention, the impedance characteristics of the overlying skin or epithelium are measured and factored in to the diagnostic interpretation of the data. For example the surface potential may be more positive (or less negative) than the reference site because of increased conductance of the overlying skin, rather than because of an underlying tumor.

The electrodes are placed over the suspicious region and the passive DC potential is measured. Then AC impedance measurements are made as discussed below. The variable impedance properties of the overlying skin may attenuate or increase the measured DC surface electropotentials. Alternatively, impedance measurements at different frequencies may initially include a superimposed continuous sine wave on top of an applied DC voltage. Phase, DC voltage and AC voltage will be measured. The resistance of the skin or other epithelium at AC and a different resistance at DC are measured. Under DC conditions since there is no phase shift we are able to measure the transepithelial potential at the surface. The capacitive properties of the skin allow the underlying breast epithelial and tumor potential to be measured at the skin surface.

Once the ECM results in "wetting" of the skin surface there is pseudo-exponential decay in the skin surface potential using the above referenced approach. Ions in the ECM diffuse through the skin and make it more conductive, particularly because of changes in the skin parallel resistance. The time constant for this decay is inversely proportional to the concentration and ionic strength of the gel. Once the skin is rendered more conductive by the ECM the capacitive coupling of the surface to the underlying potential of the tumor or the surrounding epithelium is lost so that the measured potential now reflects an offset and diffusion potential at the electrode-ECM-skin interfaces.

The use of pharmacological and/or hormonal agents, however, in combination with both impedance and DC electrical potential, provides an even more effective method for detecting abnormal pre-cancerous or cancerous breast tissue. Breast cancer develops within a background of disordered proliferation, which primarily affects the terminal ductal lobular units (TDLUs). The TDLUs are lined by epithelial cells, which maintain a TEP. In regions of up-regulated proliferation, the ducts are depolarized. The depolarization of ducts under the skin surface is capacitively coupled with the overlying skin, which results in skin depolarization. When a tumor develops in a region of up-regulated proliferation the overlying breast skin becomes further depolarized compared with other regions of the breast and the impedance of the cancerous breast tissue decreases. Electrophysiological responses in TEP and impedance change under the influence of hormones and menstrual cycle.

For example, the electrophysiological response of breast tissue to 17-β-estradiol has been observed to be different in pre-cancerous or cancerous tissue than in normal breast tissue. In one method of present invention, estradiol is introduced directly into the duct or systematically following sublingual administration of 17-β-estradiol (4 mg). This agent produces a rapid response, which peaks at approximately 20 minutes. The electrophysiological response depends, in part, on the stage of the patient's menstrual cycle, as well as the condition of the breast tissue. Specifically, in normal breast tissue, a rise in TEP will occur during the follicular (or early) phase. In pre-cancerous or cancerous tissue, this response is abrogated. Post-menopausal women at risk for breast cancer may have an exaggerated TEP response to estradiol because of up-regulated estrogen receptors on epithelial cell surfaces.

Figure 8:
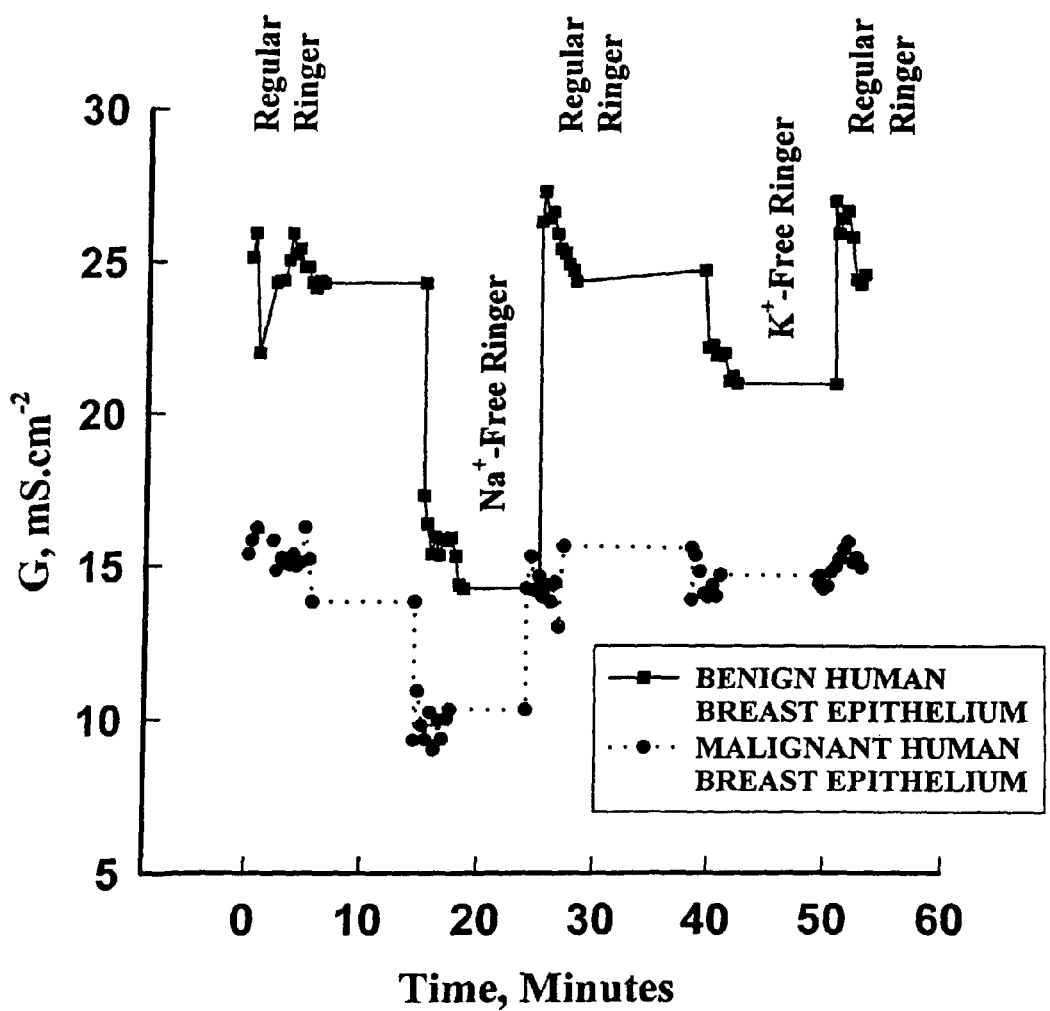
FIG. 8 illustrates varying ionic content and the effect on transepithelial conductance in human breast epithelium.

FIG. 8 demonstrates the effect of varying the ionic content of the bathing Ringers solution on transepithelial conductance. The human breast epithelial cells were grown as monolayers on Millipore filters and grew to confluence in 7 to 10 days. The epithelia were then mounted in modified Ussing chambers and the DC conductances were measured using a voltage clamp. The conductance was measured by passing a 2 µA current pulse for 200 milliseconds and measuring the DC voltage response and calculating the transepithelial conductance (y-axis), and plotting it against time α-axis). The conductance was measured first in standard Ringer solution, then in a sodium-free Ringer, then returned to standard Ringer, then in a potassium-free Ringer and finally returning to standard Ringer solution while maintaining normal osmolality during the studies.

The upper plot (filled squares and solid line) demonstrates the conductance of benign human breast epithelia grown as a monolayer. The conductance is higher in the benign epithelial cells. The $Na^+$ and $K^+$ components of conductance are approximately, 10 and 5 $mS.cm^{-2}$ respectively.

The lower plot (filled circles and dotted line) demonstrates the conductance of malignant human breast epithelia grown as a monolayer. The conductance is significantly lower in the malignant epithelial cells. The $Na^+$ and $K^+$ components of conductance are approximately, 4 and 1 $mS.cm^{-2}$ respectively.

In malignant tumors as opposed to monolayers of malignant epithelial cells the tight junction between cells break down and the tumor becomes more conductive than either benign or malignant epithelial monolayers. This observation may be exploited in the diagnosis of breast cancer. The lower conductance of the epithelium around a developing tumor, together with a region of high conductance at the site of the malignancy, may be used to more accurately diagnose breast cancer. Using electrodes with ECMs with different ionic composition will permit the specific ionic conductances to be used in cancer diagnosis. For example a high conductance region with a surrounding area of low K-conductance is indicative of breast cancer, A high conductance area with a surrounding region of normal conductance may be more indicative of fibrocystic disease (a benign process).

Figure 9:
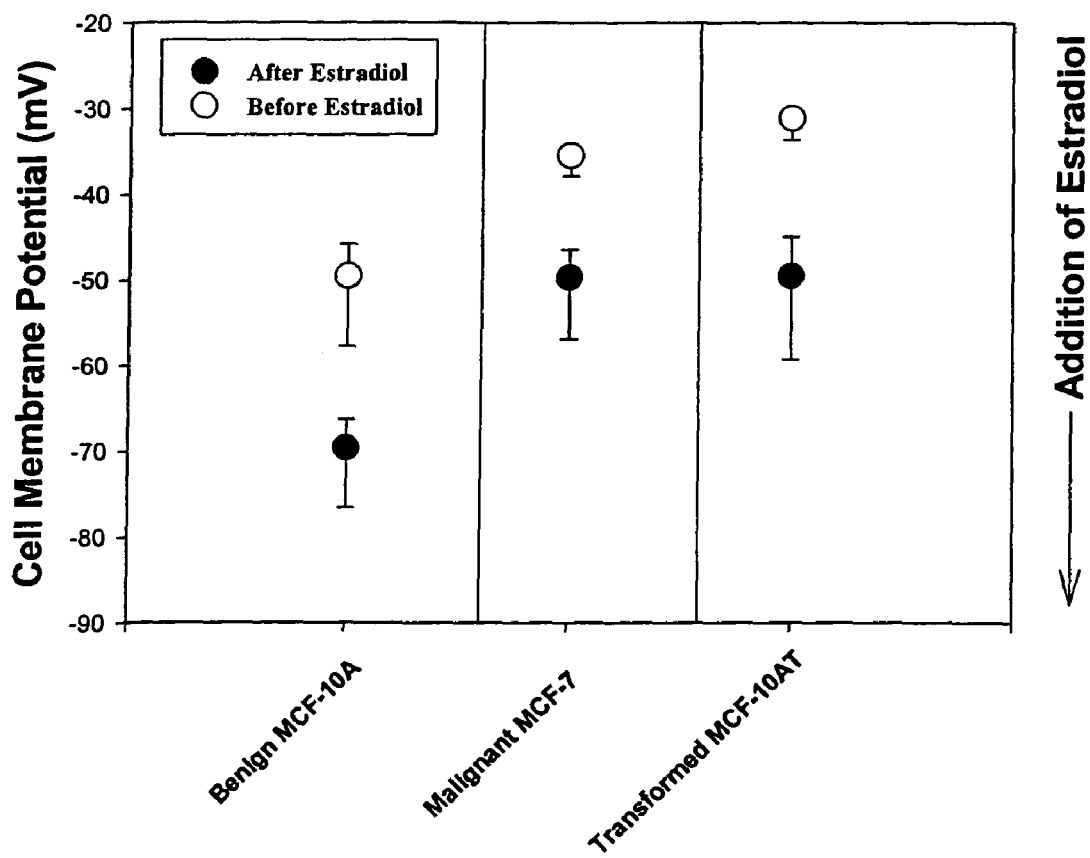
FIG. 9 illustrates measurements of cell membrane potential in human breast epithelial cells.

FIG. 9 demonstrates measurements of cell membrane potential ($\Psi$) in human breast epithelial cells. Measurements were made using a potentiometric fluorescent probe, and ratiometric measurements, which are calibrated using valinomycin and $K^+$-gradients. $\Psi$s were measured in the presence (closed circles) and absence (open circles) of estradiol (the active metabolite of estrogen). Each symbol is the mean measurement. The upper error bar is the standard error of the mean, and the lower error bar is the 95% confidence level for the observations. The addition of estrogen to cultured breast epithelial cells results in an instantaneous increase in $\Psi$ (data not shown) as well as transepithelial potential see FIG. 10. Transepithelial potential ($V_T$) of an epithelium is the sum of the apical (luminal) cell membrane potential ($V_A$) and the basolateral (abluminal) cell membrane potential ($V_{BL}$). Therefore $V_T = V_A + V_{BL}$ (changes in $V_A$ and $V_{BL}$ will therefore alter $V_T$ or transepithelial potential).

FIG. 9 demonstrates that benign breast epithelial cells have a $\Psi$ of approximately −50 mV in the absence of estradiol and −70 mV when estradiol is added to the culture media. Malignant and transformed cells have a T of between −31 and −35 mV in the absence of estradiol and approximately 50 mV when estradiol is present in the culture medium.

The difference in the electrical properties may be exploited to diagnose breast cancer in vivo. Surface electropotential measurements are a combination of the transepithelial potential, tumor potential and overlying skin potential. Physiological doses of estradiol may be administered to the patient to increase T and the sustained effect of estradiol results in an increase in transepithelial potential and tumor potential measured as an increase in surface electropotential. The increase following sustained exposure (as opposed to the instantaneous response) is less in malignant than benign breast tissue.

Figure 10:
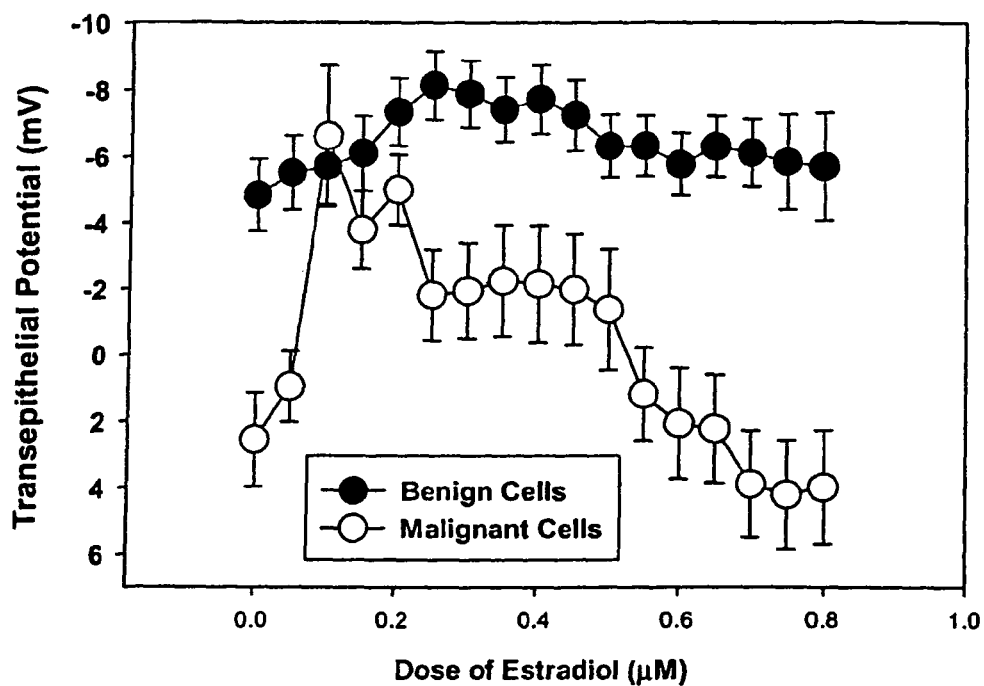
FIG. 10 illustrates the effect of increasing estradiol on the transepithelial potential in benign and malignant breast epithelia.

It should be noted that the instantaneous response, illustrated in FIG. 10, is greater in malignant epithelia, whereas the chronic or sustained exposure to estradiol results in a lower increase in TEP (transepithelial electropotential) in malignant cells. Concurrent measurement of surface electropotential and impedance allow the more accurate diagnosis of cancer. FIG. 10 demonstrates the instantaneous effect of increasing doses of estradiol on the transepithelial potential (TEP) of benign and malignant human breast epithelial cells. The cells were grown as monolayers on Millipore filters and grew to confluence in 7 to 10 days. The epithelia were then mounted in modified Ussing chambers and the TEP was measured using a voltage clamp. Increasing doses of estradiol between 0 and 0.8 µM were added α-axis). The transepithelial potential was measured after each addition and the TEP was measured (y-axis).

The different dose response is apparent for benign and malignant epithelia. Malignant epithelia have a lower TEP but undergo an instantaneous increase in TEP of approximately 9 mV (becomes more electronegative and reaches a level of <6 mV) after exposure to only 0.1 µM estradiol and then depolarize to approximately −2 mV with increasing doses of estradiol up to about 0.5 µM. Benign epithelia have a lesser response to increasing doses of estradiol and do not peak until almost 0.3 µM and then remain persistently elevated (higher electro negativity), unlike the malignant epithelia, with increasing doses of estradiol.

This difference in dose response may be exploited to diagnose breast cancer. Estradiol, or other estrogens, at a low dose will be administered systemically, transcutaneously, or by other route. The instantaneous response of the surface electropotential and impedance may then be used to diagnose breast cancer with improved accuracy over existing diagnostic modalities using impedance or DC measurement alone.

Figure 11:
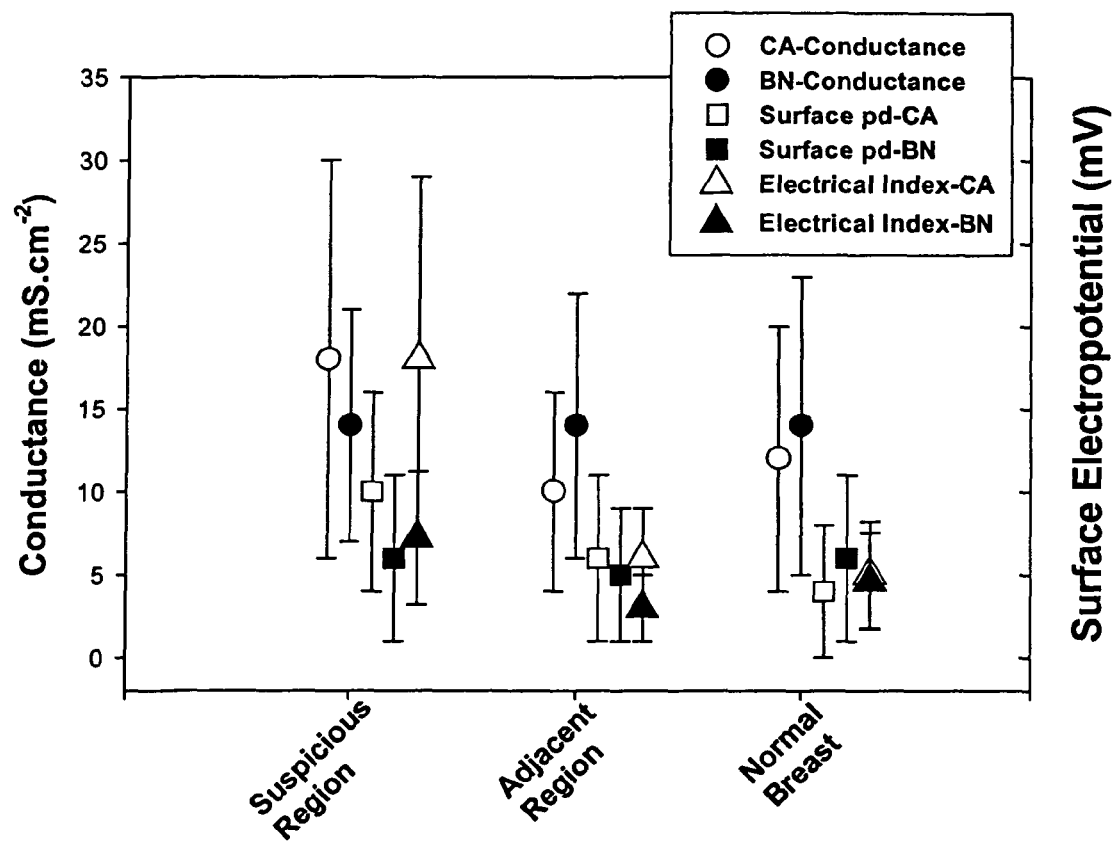
FIG. 11 illustrates conductance and electropotential measurements made over the surface of the breast in women with and without breast cancer.

FIG. 11 shows conductance measurements made at 2000 Hz at the surface of the breast. At this frequency the influence of the overlying skin impedance is less. There is still however some variable component of skin impedance, which results in significant variability of the measurement as evidenced by the overlapping error bars. Each symbol represents the median measurement with error bars the standard deviation of the mean.

Open symbols represent measurements made in patients with a biopsy proven malignancy, while closed symbols represent measurements made in patients whose subsequent biopsy proved to be a benign process such as fibrocystic disease. Malignant lesions are often associated with surrounding breast epithelium that demonstrates up-regulated proliferation. These regions ("adjacent region") are depolarized and may have a lower conductance than either over the region of malignancy. This decreased conductance may be because of decreased $K^+$-conductance of the adjacent and pre-malignant epithelium as I have observed in human colon.

Each of the three groups of symbols represents measurements from over a suspicious lesion or region, then the adjacent region, and then over normal breast in an uninvolved quadrant of the breast. The first two symbols (circles) in each of the three groups are impedance measurements where the median value is plotted against the left y-axis as conductance in $mS.cm^{-2}$. The second two symbols (squares) is the surface electrical potential measured in mV and plotted against the right y-axis; each division equals 5 mV. The third two symbols (triangles) is the electrical index for benign and malignant lesions and is in arbitrary units and is derived from the conductance and surface potential measurement. It is immediately apparent that there is less overlap in the error bars (standard deviation of the mean). Therefore breast cancer can be more accurately diagnosed using a combination of surface potential measurement and AC-impedance measurements. Further enhancements of this technique will involve the use of spaced electrodes to probe different depths of the breast, and the use of the hormones, drugs and other agents to differentially alter the impedance and transepithelial potential from benign and malignant breast tissue, and measured at the skin surface. This will enable further improvements in diagnostic accuracy.

Figure 12:
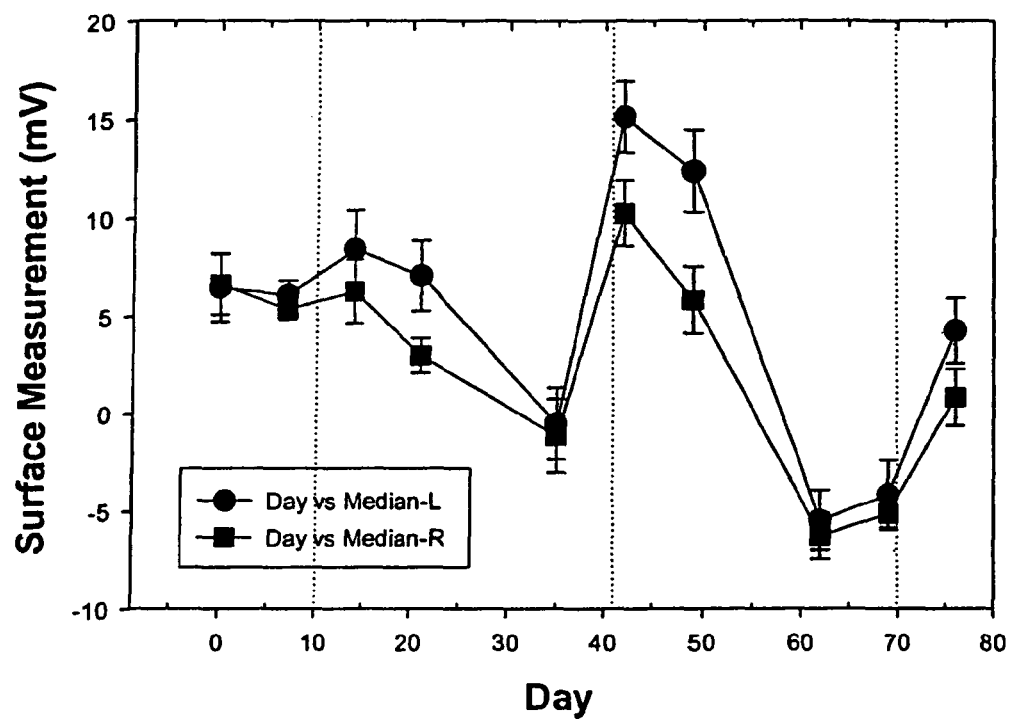
FIG. 12 illustrates the measurement of electropotential at the surface of the breast, and variation of the measurement during menstrual cycle.

It should be understood that the surface potential measurement of breast tissue varies based on the position of the woman in her menstrual cycle. FIG. 12 illustrates this variance. This figure demonstrates electropotential measurements taken over the surface of each breast at 8 different locations with an array of 8 electrodes on each breast referenced to an electrode on the skin of the upper abdomen. Measurements are taken with error bars equal to the standard error of the mean. Filled circles and filled squares represent the median value from the left and right breast respectively. The vertical dotted line is the first day of each menstrual cycle.

It can be seen that the median values for each breast tend to track one another with lower values in the first half of menstrual cycle (follicular phase) and higher values in the latter part of cycle (luteal phase). Although the measured electrical values are not completely superimposed, because of other factors affecting the electropotential of the breast, it can be seen that the lowest levels of electropotential are observed 8-10 days before menstruation and the rise to the highest levels around the time of menstruation. This may be because estradiol levels are higher in the second part of menstrual cycle and directly affect breast surface electropotential.

The cyclical pattern of electropotential activity when a breast cancer or proliferative lesion is present is quite different. Similarly higher levels of surface electropotential are observed when measurements were made in the afternoon compared with the morning. This information can be exploited in a number of different ways. Measurement of the surface potential and impedance at different times during cycle enables a more accurate diagnosis because of a different cyclical change in surface electropotential (i.e., the peak to peak change in potential is less over a malignant region, relative to normal areas of the breast). Secondly, estradiol or another agent that changes the electropotential of the breast may be administered systemically, topically (transdermal), or by other means, and the drug or hormone-induced change in surface potential may be used as a provocative test to diagnose breast cancer.

In these ways breast cancer can be more accurately diagnosed using a combination of surface potential measurement and AC-impedance measurements.

EXAMPLE 3

Nasopharyngeal Cancer

Using methods similar to those described with respect to colon cancer, it is possible to use pharmacological and hormonal agents to enhance electrophysiological alterations caused by nasopharyngeal cancer. One exemplary method would be a nasopharyngeal probe that would include wells providing for varying concentrations of $K^+$ and would perform simple DC measurements.

EXAMPLE 4

Prostate

Figure 13:
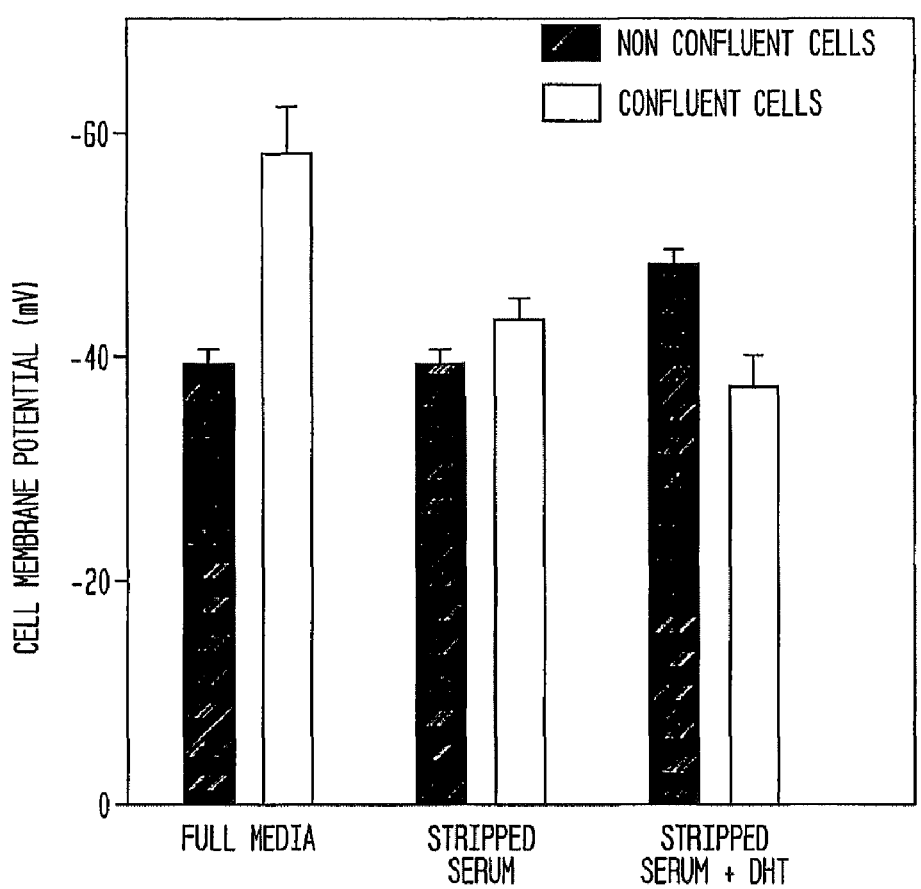
FIG. 13 illustrates measurements of cell membrane potential in human prostatic epithelial cell under different growth conditions.

FIG. 13 represent measurements of cell membrane potential ($\psi$) in human prostatic epithelial cells under different growth conditions. A Voltage-sensitive FRET (fluorescent energy transfer) probe was used for potentiometric ratio measurements. It has two fluorescent components: $CC_2$-DMPE (Coumarin) and $DISBAC_2(3)$ (Oxonol). The oxonol distributes itself on opposite sides of the cell membrane in a Nernstian manner according to the $\psi$. The voltage sensitive distribution of oxonol is transduced through a ratiometric fluorescence signal via the coumarin which is bound to the outside surface of the cell membrane thereby amplifying the fluorescence. Measurements were made using a fluorescence microscope and a digital imaging system. The ratio measurements are calibrated using Gramicidin D to depolarize the cell membrane and then varying the external $K^+$-concentration. The calibrated cell membrane potential in mV is depicted on the y-axis.

The filled bars indicates the $\psi$ of exponentially growing prostatic epithelial cells before they reach confluence, whereas the open bars depict the $\psi$ of the cells once they reach confluence and cell growth slows. The first two bars demonstrate that prostatic epithelial cells are depolarized when rapidly growing and hyperpolarize by about 20 mV when they reach confluence. The second pair of bars demonstrate that exponentially growing cells are depolarized even in growth factor deprived culture conditions (stripped serum) and hyperpolarize less in the absence of growth factors on reaching confluence. The final pair of bars demonstrate that cells grown in the presence of the active metabolite of testosterone, DHT (dihydroxytestosterone), are slightly hyperpolarized during exponential growth, but depolarize on reaching confluence.

These differences in cell membrane potential support the notion that growth conditions of prostatic epithelia in vivo will likely influence the cell membrane potential of prostatic epithelial cells. Cell membrane potential will influence the transepithelial potential measured at the prostate surface. Alteration in the DC potential measured trans-rectally in combination with impedance will be used to diagnose prostate cancer.

Figure 14:
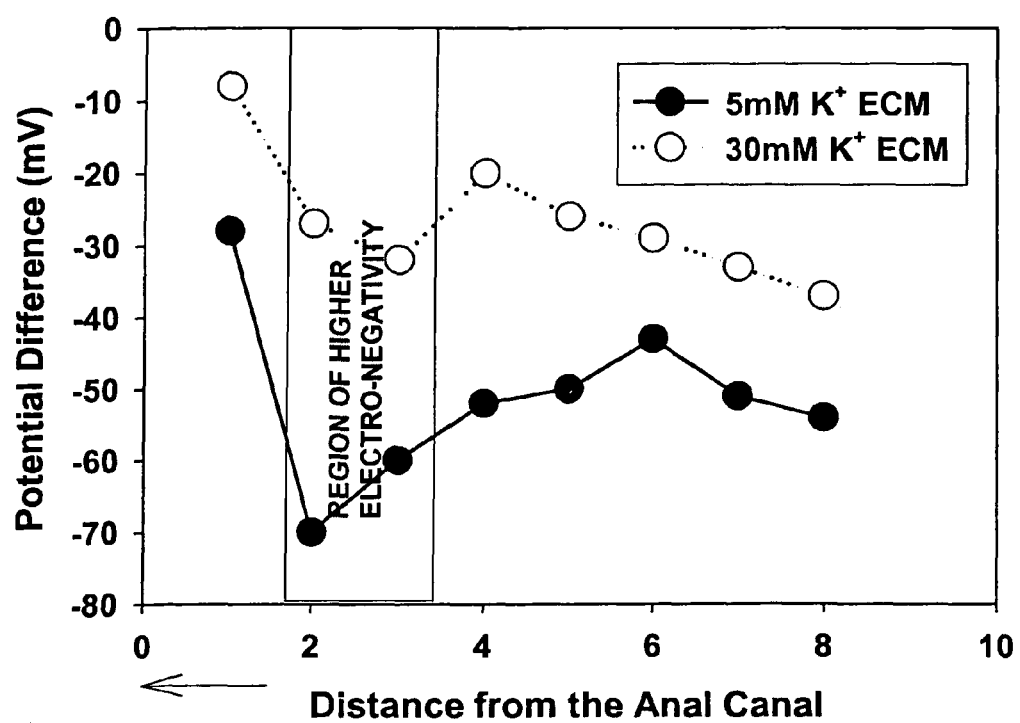
FIG. 14 illustrates measurements of electropotential in a patient with normal prostate.

FIG. 14 demonstrates electropotential measurement made over the prostate of a patient with a normal prostate. The patient was undergoing a colonoscopy for screening, which was negative and had a normal PSA. The ECM (electroconductive medium) contained 5 mM $K^+$ and physiological concentrations of other electrolytes. The filled circles and solid line represent the measurement of surface electropotential (y-axis) starting at 1 cm from the anal verge to 8 cm along the anterior aspect of the rectum (x-axis). The values increase from approximately −28 mV to −70 mV over the prostate and drop (depolarize) to approximately −52 mV over the top of the prostate, and referenced to the bloodstream. When the ECM is changed to a solution with the same osmolality, but with a $K^+$ concentration of 30 mM. The electropotential of the surface of the rectal mucosa depolarizes to 30 mV (open circles joined by a dotted line). This indicates significant $K^+$ permeability of the overlying rectal mucosa. The higher region of electro-negativity over the prostate is consistently seen when the prostate is healthy.

Figure 15:
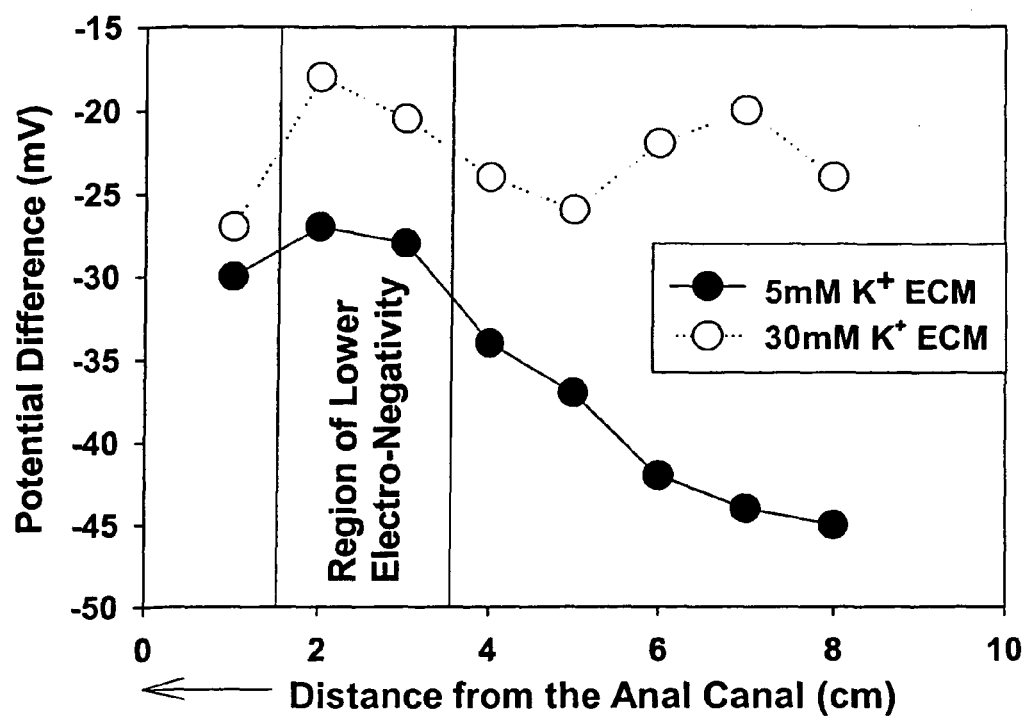
FIG. 15 illustrates measurements of electropotential in a patient with prostate cancer.

FIG. 15 demonstrates measurement made in a patient with a previously biopsied prostate cancer. The symbols and axes are the same as in FIG. 14. The region of electro-negativity is lower over the cancerous prostate. In this case electropotential measurements of between −26 and −27 mV were made over the cancerous lobe of the prostate i.e., 30 to 40 mV lower than observed over healthy prostate. When the ECM was changed to a solution with a $K^+$-concentration of 30 mM a depolarization of 8-9 mV was observed, or about a third of that observed in healthy prostate. This indicates a decrease in $K^+$-conductance and permeability of both the prostate and overlying rectal mucosa.

These changes in the normal DC electrical profile of the prostate will be used separately or in combination with AC impedance measurements to diagnose prostate cancer. Identification of depolarization of the prostate relative to the higher polarity of the surrounding rectal mucosa together with decreased $K^+$-conductance indicate the presence of prostate cancer. Additional AC measurements with differently spaced electrodes will permit probing of the underlying prostate to accurately localize the site of the prostatic malignancy.

EXAMPLE 5

Chemopreventative and Therapeutic Use

In addition to the ionic, pharmacologic, and hormonal agents described above, the system and method of the present invention may be used with cancer preventative and therapeutic agents and treatments. Specifically, electrical measurement of altered structure and function provides a method for evaluating a patient's response to the drugs without requiring a biopsy and without waiting for the cancer to further develop. Patients who respond to a given chemopreventative or therapeutic agent would likely show restoration of epithelial function to a more normal state. Patients who do not respond would show minimal change or may even demonstrate progression to a more advanced stage of the disease. This system and method, thus, may be used by either clinicians or drug companies in assessing drug response or by clinicians in monitoring the progress of a patient's disease and treatment, or monitoring the process of carcinogenesis (cancer development), before an overt malignancy has fully developed.

Furthermore an understanding of the physiological basis of the altered impedance permits more accurate diagnosis. For example impedance may increase or decrease because of several factors. Increased stromal density of breast tissue may alter impedance. This is a non-specific change, which may not have any bearing on the probability of malignancy. On the other hand a decrease in potassium permeability of the epithelia around a developing malignancy would increase impedance and would be more likely associated with a developing cancer than a non-specific impedance change. Additional information is obtained from my method by probing the tissue to different depths using spaced voltage-sensing electrodes. The use of electrophysiological, pharmacological and hormonal manipulations to alter impedance differentially in normal compared to cancer-prone, pre-malignant or malignant tissue is another significant difference, which enhances the diagnostic accuracy of my invention over the above referenced one.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A method for determining a condition of ductal epithelial tissue of the breast comprising:
   (A) placing at least one current-passing electrode in contact with or in proximity to a surface of the breast, at least one of said current-passing electrode is in electrical communication with said ductal epithelium;
   (B) placing a plurality of measuring electrodes in contact with or in proximity to said surface;
   (C) establishing an electrical signal between said at least one current-passing electrode and at least one of said measuring electrodes;
   (D) measuring, at one or more of said measuring electrodes, an impedance associated with said signal;
   (E) introducing at least one agent into said ductal epithelial tissue so as to instantaneously reveal and accentuate changes in impedance in said ductal epithelial tissue and measuring, at one or more of said measuring electrodes, an impedance associated with said signal following the introduction of said at least one agent; and
   (F) determining the condition of said ductal epithelial tissue based on said impedance.

2. The method of claim 1, wherein placing of the current-passing electrode includes the step of:
   placing a probe in contact with or in proximity to said surface, wherein said current-passing electrode is situated on said probe.

3. The method of claim 1, wherein placing of the measuring electrodes includes the step of:
   placing a probe in contact with or in proximity to said surface, wherein said measuring electrodes are situated on said probe.

4. The method of claim 1, wherein
   said at least one agent is introduced into said ductal epithelial tissue via a nipple cup electrode.

5. The method of claim 1, wherein step (A) comprises:
   placing at least two current-passing electrodes in contact with or in proximity to said surface.

6. The method of claim 5, further including the steps of:
   (G) introducing at least one agent into said epithelial tissue so as to instantaneously reveal and accentuate changes in impedance in said epithelial tissue and measuring, at one or more of said measuring electrodes, an impedance associated with said signal following the introduction of said at least one agent; and
   (H) determining the condition of said tissue based on said impedance, following the introduction of said at least one agent.

7. The method of claim 5, wherein placing of the measuring electrodes includes the step of:

placing a probe in contact with or in proximity to said surface, wherein said measuring electrodes are situated on said probe.

8. The method of claim 5, wherein the step of determining the condition of said tissue includes:
rating the tissue based on one of the following ratings: normal, at-risk, pre-cancerous, or cancerous.

9. A method for measuring electrical properties of ductal epithelial tissue of the breast, said breast having a surface, using a combination of DC electrical measurements and impedance spectroscopy, comprising the steps of:
(A) measuring a DC potential at the surface of the ductal epithelial tissue with a first and a second voltage-measuring electrode, wherein said voltage-measuring electrodes are spaced apart from one another and associated with a reference point;
(B) placing a pair of current-passing electrodes in contact with or in proximity to said ductal epithelial tissue;
(C) detecting, via said voltage-measuring electrodes, an electrical signal at different points on said epithelial tissue;
(D) applying an electrical signal to said pair of current-passing electrodes at a plurality of frequencies at said different points on said epithelial tissue;
(E) monitoring an electrical signal at said voltage-measuring electrodes associated with each of said plurality of frequencies;
(F) determining impedance of said epithelial tissue associated with the voltage-measuring electrodes based on each of the plurality of frequencies;
wherein said reference point includes an intravenous electrode or a skin electrode with low skin impedance and wherein at least one of which electrodes is in electrical communication with said ductal epithelium.

10. The method of claim 9, wherein the applied electrical signal includes low and high frequency sinusoidal alternating currents.

11. The method of claim 10, wherein the sinusoidal alternating currents are applied sequentially.

12. The method of claim 9 further including the steps of:
(G) introducing at least one agent into said region of epithelial tissue so as to instantaneously reveal and accentuate changes in: (i) DC potential; or (ii) impedance; or both (i) and (ii) in said epithelial tissue following the introduction of said at least one agent;
(H) measuring, at one or more of said voltage-measuring electrodes, a DC potential at the surface of the epithelial tissue as in (A) and impedance associated with said signal as in (D), (E) and (F) following the introduction of said at least one agent; and
(I) determining the condition of said region of epithelial tissue based on the change in said DC potential and said impedance following the introduction of said at least one agent.

13. The method of claim 9, wherein the resulting electrical signal is a real part of a resulting potential difference measured over a current path across the current-passing electrodes.

14. The method of claim 9, wherein the plurality of frequencies falls within the range of 0.2-6000 Hz.

15. The method of claim 9, wherein the plurality of frequencies falls within the range of 2 to 800 kHz.

16. The method of claim 9, further including a modified nipple cup adapted to receive at least one of said electrodes in order to facilitate electrical contact with the ductal epithelium of the breast.

17. The method of claim 9, further including the step of:
reducing a DC component of the resulting signal using a band-pass filter.

18. A method for measuring electrical properties of ductal epithelial tissue of the breast, said breast having a surface, using a combination of DC electrical measurements and impedance spectroscopy, comprising the steps of:
(A) measuring a DC potential of the ductal epithelial tissue with a first and a second voltage-measuring electrodes, wherein the voltage-measuring electrodes are associated with a reference point;
(B) placing at least one current-passing electrode in contact with or in proximity to said ductal epithelial tissue;
(C) detecting, via said voltage-measuring electrodes, a resulting electrical signal at different points on said epithelial tissue;
(D) applying an electrical signal to at least one of said current-passing electrodes and at least one of the voltage-measuring electrodes at a plurality of frequencies at said different points on said epithelial tissue;
(E) monitoring an electrical signal at said voltage-measuring electrodes associated with each of said plurality of frequencies;
(F) determining impedance of said region of epithelial tissue associated with said voltage-measuring electrodes based on each of said plurality of frequencies and said resulting electrical signal associated with each of said plurality of frequencies;
(G) introducing at least one agent into said region of ductal epithelial tissue so as to instantaneously reveal and accentuate changes in: (i) DC potential; or (ii) impedance; or both (i) and (ii) in said epithelial tissue following the introduction of said at least one agent;
(H) measuring, at one or more of said voltage-measuring electrodes, a DC potential of the epithelial tissue as in (A) and impedance associated with said signal as in (D), (E) and (F) following the introduction of said at least one agent; and
(I) determining a condition of said region of ductal epithelial tissue based on said change step (G).

19. An apparatus for determining the condition of tissue of a ductal epithelium of the breast using a combination of surface DC electrical measurements and impedance spectroscopy and specific ionic conductance, the apparatus comprising:
(A) a first pair of spaced electrodes for applying an electrical signal to the ductal epithelium;
(B) a second pair of spaced electrodes for detecting an electrical signal at different points on the ductal epithelium;
(C) a means for applying the electrical signal to the first pair of electrodes at a plurality of frequencies;
(D) a means for measuring an electrical signal at the second pair of electrodes at said plurality of frequencies;
(E) a means for obtaining a measure of the impedance of a part of the ductal epithelium based on said electrical signal in (D); and
(F) a means for obtaining a difference signal representing a change in impedance with frequency,
wherein each electrode of the second pair of electrodes includes an electroconductive medium concentration that differs from the other for estimating said specific ionic conductance of said epithelium.

20. The apparatus of claim 19, further comprising:
one or more additional pairs of electrodes placed at different locations than said first or second pairs of electrodes; and a means for measuring a resulting electrical signal between said additional pairs of electrodes; and a means for estimating an impedance for different layers of said ductal epithelium by subtracting the impedance values from two pairs of said electrodes at each frequency.

21. The apparatus of claim 19, wherein said means for applying said electric signal includes:

a signal generator for producing simultaneously a plurality of low and high frequency constant alternating current signals; and a connection means for supplying such signals to said first pair of electrodes.

22. The apparatus of claim 19, wherein the means for measuring the resulting electrical signal includes:

at least one adjustable gain voltage amplifier.

23. The apparatus of claim 19, wherein said means for obtaining the difference signal includes a microprocessor computing device.

24. The apparatus of claim 23, wherein said microprocessor computing device includes a low-pass filter.

25. The apparatus of claim 23, wherein said microprocessor computing device includes at least one of a band-pass filter and a high pass filter.

* * * * *

UNITED STATES PATENT AND TRADEMARK OFFICE
CERTIFICATE OF CORRECTION

PATENT NO. : 8,280,504 B2  
APPLICATION NO. : 11/096665  
DATED : October 2, 2012  
INVENTOR(S) : Richard J. Davies Page 1 of 1

It is certified that error appears in the above-identified patent and that said Letters Patent is hereby corrected as shown below:

In the Claims

At column 26, line 40, after "change" insert --in--.

Signed and Sealed this
Twenty-ninth Day of April, 2014

Michelle K. Lee
*Deputy Director of the United States Patent and Trademark Office*